US012694529B2

(12) United States Patent
Takenouchi

(10) Patent No.: US 12,694,529 B2
(45) Date of Patent: Jul. 28, 2026

(54) MEDICAL IMAGE PROCESSING APPARATUS, METHOD FOR OPERATING MEDICAL IMAGE PROCESSING APPARATUS, AND NON-TRANSITORY COMPUTER READABLE MEDIUM FOR DETERMINING A MEDICAL IMAGE OF INTEREST BASED ON DEGREE OF INTEREST TO A USER

(71) Applicant: FUJIFILM Corporation, Tokyo (JP)

(72) Inventor: Seiya Takenouchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 572 days.

(21) Appl. No.: 18/183,801

(22) Filed: Mar. 14, 2023

(65) Prior Publication Data

US 2023/0222666 A1 Jul. 13, 2023

Related U.S. Application Data

(63) Continuation of application No. PCT/JP2021/033708, filed on Sep. 14, 2021.

(30) Foreign Application Priority Data

Sep. 15, 2020 (JP) ................................. 2020-154662

(51) Int. Cl.
*G06T 7/00* (2017.01)
*A61B 1/00* (2006.01)
(Continued)

(52) U.S. Cl.
CPC ...... *G06T 7/0016* (2013.01); *A61B 1/000094* (2022.02); *A61B 1/00045* (2013.01);
(Continued)

(58) Field of Classification Search
CPC ......... G06T 7/0016; G06T 2207/10068; G06T 2207/30096; G06T 7/70; G06T 7/90;
(Continued)

(56) References Cited

U.S. PATENT DOCUMENTS

2012/0183188 A1* 7/2012 Moriya .................. G16H 30/20
382/128
2012/0195482 A1* 8/2012 Wakai ................ G01R 33/5608
382/128
(Continued)

FOREIGN PATENT DOCUMENTS

JP 2013-128702 A 7/2013
JP 2015-173827 A 10/2015
(Continued)

OTHER PUBLICATIONS

An Office Action; "Notice of Reasons for Refusal," mailed by the Japanese Patent Office on Feb. 27, 2024, which corresponds to Japanese Patent Application No. 2022-550561 and is related to U.S. Appl. No. 18/183,801; with English language translation.
(Continued)

*Primary Examiner* — Allen H Nguyen
(74) *Attorney, Agent, or Firm* — Studebaker Brackett PLLC

(57) ABSTRACT

An endoscopic image viewing support server includes an endoscopic image acquiring unit configured to acquire imaging information, a section-of-interest setting unit configured to estimate a degree of interest and classify a plurality of endoscopic images in accordance with the degree of interest,
(Continued)

and an endoscopic image selecting unit configured to select an endoscopic image from each of sections of interest at a ratio based on the degree of interest. The section-of-interest setting unit is configured to determine an endoscopic image of interest from among the plurality of endoscopic images, and in a case where the plurality of endoscopic images are arranged in a chronological order, estimate the degree of interest for an endoscopic image in an endoscopic image group including the endoscopic image of interest by using image processing.

14 Claims, 21 Drawing Sheets

(51) Int. Cl.
    *A61B 1/05* (2006.01)
    *A61B 90/00* (2016.01)
(52) U.S. Cl.
    CPC ......... *A61B 1/05* (2013.01); *A61B 2090/0803* (2016.02); *G06T 2207/10068* (2013.01); *G06T 2207/30096* (2013.01)
(58) Field of Classification Search
    CPC . G06T 2207/10016; G06T 2207/10024; G06T 2207/10072; G06T 2207/10116; G06T 2207/10132; G06T 2207/20084; G06T 2207/30101; G06T 7/0012; A61B 1/000094; A61B 1/00045; A61B 1/05; A61B 2090/0803; A61B 1/000095; A61B 1/00188; A61B 1/0005; A61B 1/0638; G16H 15/00; G16H 50/20; G16H 30/20; G16H 30/40
    USPC .......................................................... 382/128
    See application file for complete search history.

(56) References Cited

U.S. PATENT DOCUMENTS

| | | | | |
|---|---|---|---|---|
| 2015/0051489 A1* | 2/2015 | Caluser | .................... | A61B 8/13 |
| | | | | 600/440 |
| 2015/0317434 A1* | 11/2015 | Kondo | ................... | A61B 6/463 |
| | | | | 705/3 |
| 2015/0356734 A1* | 12/2015 | Ooga | ..................... | A61B 6/486 |
| | | | | 382/131 |
| 2016/0110584 A1* | 4/2016 | Remiszewski | ......... | G06V 20/69 |
| | | | | 382/133 |
| 2016/0379363 A1* | 12/2016 | Kitamura | ............. | A61B 1/0005 |
| | | | | 600/371 |
| 2017/0004620 A1 | 1/2017 | Kitamura et al. | | |
| 2017/0004625 A1 | 1/2017 | Kamiyama et al. | | |
| 2017/0055929 A1* | 3/2017 | Machida | .............. | A61B 6/5235 |
| 2019/0087959 A1 | 3/2019 | Kitamura et al. | | |
| 2020/0008653 A1 | 1/2020 | Kamon | | |
| 2020/0258224 A1 | 8/2020 | Endo | | |
| 2021/0042926 A1 | 2/2021 | Usuda | | |
| 2025/0157028 A1* | 5/2025 | Watanabe | ........ | A61B 1/000096 |

FOREIGN PATENT DOCUMENTS

| | | |
|---|---|---|
| JP | 2015-173921 A | 10/2015 |
| JP | 2015-181594 A | 10/2015 |
| WO | 2017/199408 A1 | 11/2017 |
| WO | 2018/179991 A1 | 10/2018 |
| WO | 2019/082741 A1 | 5/2019 |
| WO | 2019/220801 A1 | 11/2019 |

OTHER PUBLICATIONS

International Search Report issued in PCT/JP2021/033708; mailed Nov. 30, 2021.
International Preliminary Report On Patentability (Chapter I) and Written Opinion of the International Searching Authority issued in PCT/JP2021/033708; issued Mar. 21, 2023.

* cited by examiner

1

MEDICAL IMAGE PROCESSING APPARATUS, METHOD FOR OPERATING MEDICAL IMAGE PROCESSING APPARATUS, AND NON-TRANSITORY COMPUTER READABLE MEDIUM FOR DETERMINING A MEDICAL IMAGE OF INTEREST BASED ON DEGREE OF INTEREST TO A USER

CROSS-REFERENCE TO RELATED APPLICATIONS

This application is a Continuation of PCT International Application No. PCT/JP2021/033708 filed on 14 Sep. 2021, which claims priority under 35 U.S.C § 119(a) to Japanese Patent Application No. 2020-154662 filed on 15 Sep. 2020. The above application is hereby expressly incorporated by reference, in its entirety, into the present application.

BACKGROUND OF THE INVENTION

1. Field of the Invention

The present invention relates to a medical image processing apparatus that performs image processing on a medical image, a method for operating the medical image processing apparatus, and a non-transitory computer readable medium.

2. Description of the Related Art

In the medical field, image diagnosis is performed for diagnosing a disease of a patient, performing follow-up, or the like by using medical images, such as endoscopic images, X-ray images, computed tomography (CT) images, or magnetic resonance (MR) images. A doctor or the like determines a course of treatment on the basis of such image diagnosis.

In recent image diagnosis using medical images, a medical image processing apparatus automatically selects a representative endoscopic image from among a plurality of medical images acquired in the unit of one examination, and the selected medical image is used for image diagnosis or examination report.

JP2015-181594A (corresponding to US2017/004625A1) describes a medical image processing apparatus that detects abnormal images including an abnormal region from a medical image group acquired in the unit of examination, extracts abnormal images included in a chronological proximity range as an abnormal image group, and selects an abnormal image including an abnormal region with a high degree of importance or an abnormal image with good visibility of an abnormal region from the abnormal image group by image processing.

SUMMARY OF THE INVENTION

In the case of medical images for performing image diagnosis described above, particularly in the case of an endoscopic examination, a very large number of endoscopic images are acquired in the unit of examination, and a large burden is imposed on a doctor who makes a selection. Thus, there is a demand for efficiently selecting a medical image.

However, in the medical image processing apparatus described in JP2015-181594A, image processing is used to select a medical image, but no consideration is given to information regarding capturing of a medical image, for example, a capturing time, information on a lesion portion detected at the time of imaging, whether treatment with a treatment tool is performed, position information, and so forth, and actions taken by a doctor are not reflected. Thus, a medical image not desired by the doctor may be selected in medical image selection. If the medical image is not desired by the doctor, the doctor eventually has to manually select a medical image, which makes it impossible to reduce the burden on the doctor.

In the medical image processing apparatus described in JP2015-181594A, the number of medical images to be selected is a predetermined number or a number proportional to abnormal images, and medical images are selected only from an abnormal image group in which an abnormal region has been detected. The number of medical images to be selected varies according to the policy of a doctor or a hospital, and a medical image having no abnormal region detected may be selected.

An object of the present invention is to provide a medical image processing apparatus capable of making a selection from a plurality of medical images with high accuracy and at an appropriate ratio, a method for operating the medical image processing apparatus, and a non-transitory computer readable medium.

The present invention is a medical image processing apparatus including a processor configured to acquire imaging information that has a plurality of medical images captured by a user and that has accessory information recorded in association with each medical image; estimate, from the imaging information, a degree of interest of the user when the medical image is captured, and set sections of interest to which the plurality of medical images are classified in accordance with the degree of interest; and select a medical image from each section of interest at a ratio that is based on the degree of interest. The processor is configured to determine a medical image of interest from among the plurality of medical images on the basis of the imaging information, and in a case where the plurality of medical images are arranged in a chronological order, estimate the degree of interest for at least one medical image in a medical image group including the medical image of interest by using image processing.

Preferably, the processor is configured to, in the estimation of the degree of interest using image processing, use, as the degree of interest, a degree of similarity with preceding and subsequent medical images in an arrangement in a chronological order.

Preferably, the processor is configured to determine a medical image including an abnormal region to be the medical image of interest, and in the estimation of the degree of interest using image processing, use, as the degree of interest, a degree of abnormality of the abnormal region.

Preferably, the processor is configured to determine a medical image including an abnormal region to be the medical image of interest, and in the estimation of the degree of interest using image processing, use, as the degree of interest, a state of treatment for the abnormal region.

Preferably, the processor is configured to acquire, from the accessory information, a capturing time at which the medical image is captured, and in addition to perform the estimation of the degree of interest using image processing, use, as the degree of interest, a value inversely proportional to a capturing interval with respect to preceding and subsequent medical images in an arrangement in a chronological order.

Preferably, the medical image is an endoscopic image captured by an imaging sensor of an endoscope. Preferably, the accessory information has, recorded therein, position information indicating a position in a subject where the imaging sensor is located when the medical image is captured, and a capturing time at which the medical image is captured. Preferably, the processor is configured to acquire the position information and the capturing time, and use, as the degree of interest, a length of a stay time during which the imaging sensor stays at the same position when the medical image is captured.

Preferably, the medical image is an endoscopic image captured by an imaging sensor of an endoscope. Preferably, the accessory information has, recorded therein, position information indicating a position in a subject where the imaging sensor is located when the medical image is captured. Preferably, the processor is configured to count, using the position information, the number of times of capturing in which the imaging sensor captures the medical image at the same position, and use the number of times of capturing as the degree of interest.

Preferably, the accessory information is wavelength range information of a light source used to capture the medical image, and the processor is configured to estimate the degree of interest from the wavelength range information.

Preferably, the processor is configured to acquire the medical image and the accessory information, the medical image being captured by the user operating a device. Alternatively, the processor may be configured to acquire the medical image and the accessory information, the medical image being automatically captured without the user operating a device.

Preferably, the processor is configured to select the medical image within a range not exceeding the number of images designated by the user. Preferably, the processor is configured to display the selected medical image in an order that is based on the degree of interest. Preferably, the processor is configured to store the selected medical image in a storage device.

A method for operating a medical image processing apparatus of the present invention includes a step of acquiring imaging information that has a plurality of medical images captured by a user and that has accessory information recorded in association with each medical image; a step of estimating, from the imaging information, a degree of interest of the user when the medical image is captured, and setting sections of interest to which the plurality of medical images are classified in accordance with the degree of interest; a step of selecting a medical image from each section of interest at a ratio that is based on the degree of interest; and a step of determining a medical image of interest from among the plurality of medical images on the basis of the imaging information, and in a case where the plurality of medical images are arranged in a chronological order, estimating the degree of interest for at least one medical image in a medical image group including the medical image of interest by using image processing.

A non-transitory computer readable medium of the present invention stores a computer-executable program for performing image processing on a medical image. The computer-executable program causes a computer to implement a function of acquiring imaging information that has a plurality of medical images captured by a user and that has accessory information recorded in association with each medical image; a function of estimating, from the imaging information, a degree of interest of the user when the medical image is captured, and setting sections of interest to which the plurality of medical images are classified in accordance with the degree of interest; a function of selecting a medical image from each section of interest at a ratio that is based on the degree of interest; and a function of determining a medical image of interest from among the plurality of medical images on the basis of the imaging information, and in a case where the plurality of medical images are arranged in a chronological order, estimating the degree of interest for at least one medical image in a medical image group including the medical image of interest by using image processing.

According to the present invention, it is possible to make a selection from a plurality of medical images with high accuracy and at an appropriate ratio.

BRIEF DESCRIPTION OF THE DRAWINGS

FIG. 10 is a block diagram illustrating an electrical configuration of a computer used for an endoscopic image viewing support server or the like;

DESCRIPTION OF THE PREFERRED EMBODIMENTS

First Embodiment

Figure 1:
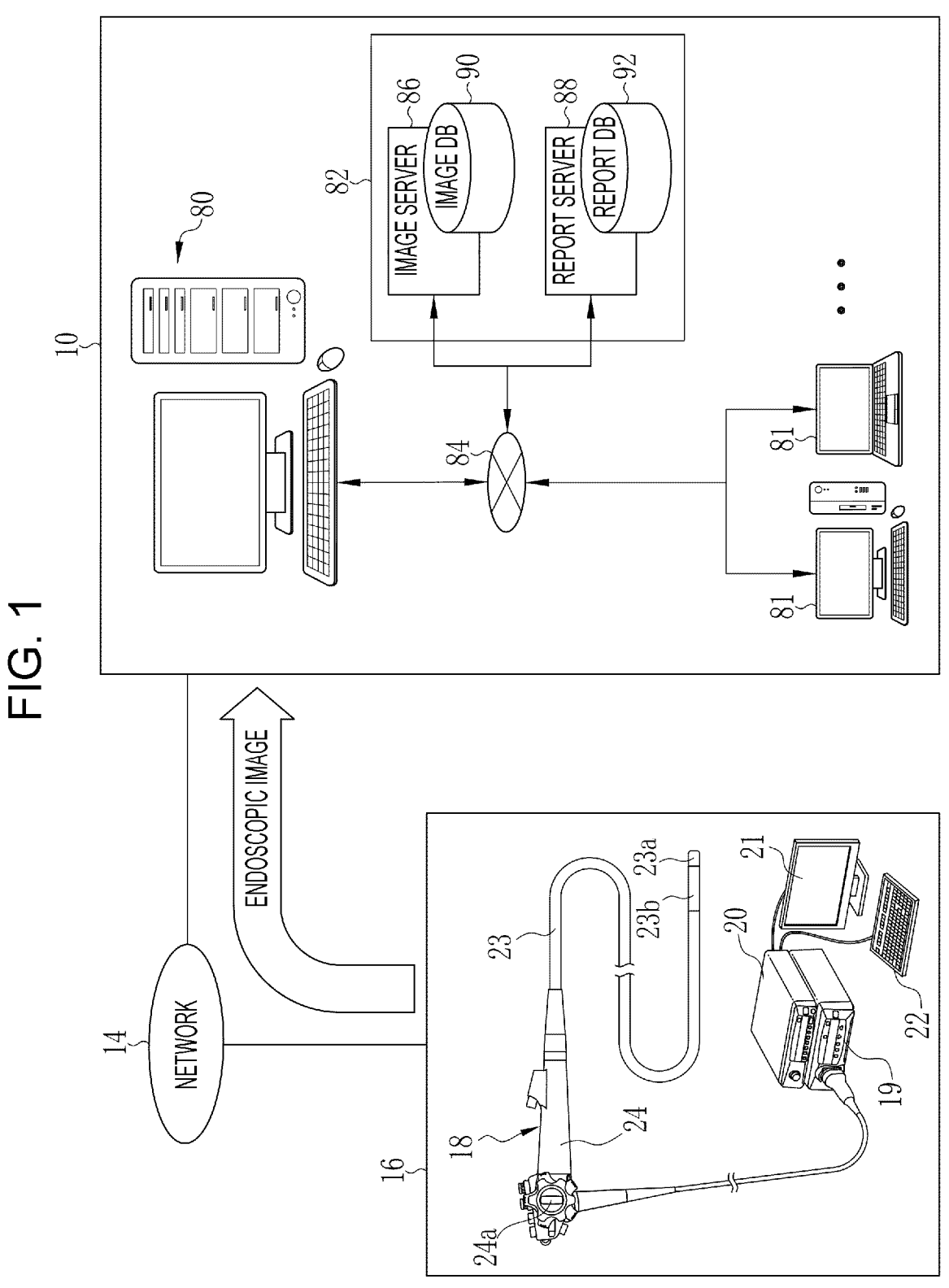
FIG. 1 is an explanatory diagram illustrating an overview of the configuration of an endoscopic image viewing support system.

An endoscopic image viewing support system 10 illustrated in FIG. 1 is a computer system used to support viewing of endoscopic images 100 (see FIG. 7 and so forth) acquired in an endoscopic examination, and is connected to an endoscope system 16 via a network 14. The network 14 is, for example, a local area network (LAN) in a hospital.

The endoscope system 16 is used for endoscopic examinations (including various treatments using an endoscope 18). An endoscopic examination is performed by, for example, an examination doctor who has received a request from a doctor in charge of a patient. A plurality of endoscopic images 100 are acquired by performing the endoscopic examination, as will be described below.

In the endoscopic image viewing support system 10 of the present embodiment, an endoscopic image viewing support server 80, which will be described below, selects one or some of the plurality of endoscopic images 100, generates an endoscopic image display screen 104 for displaying the endoscopic images 100, and creates an examination report 94 (see FIG. 9) having the selected endoscopic images 100 attached thereto. The examination report 94 and the endoscopic images 100 acquired in the endoscopic examination are provided for viewing by the doctor in charge of the patient and used for diagnosis of the patient, for example.

Configuration of Endoscope System

The endoscope system 16 includes the endoscope 18, a light source apparatus 19, a processor apparatus 20, a display 21, and a console 22. The endoscope 18 includes an insertion section 23 to be inserted into the body of a patient, and an operation section 24 provided at a base end portion of the insertion section 23. A distal end portion 23*a* and a bending portion 23*b* are provided on the distal end side of the insertion section 23. Operating of an angle knob 24*a* provided in the operation section 24 causes the bending portion 23*b* to perform a bending operation. The bending operation causes the distal end portion 23*a* to be directed in a desired direction.

The distal end portion 23*a* has, on the distal end surface thereof, an illumination window, an observation window, an air/water supply nozzle, and a forceps port (any of them is not illustrated). The illumination window is for irradiating an observation portion with illumination light. The observation window is for capturing light from the observation portion. The air/water supply nozzle is for washing the illumination window and the observation window. The forceps port is for performing various treatments by using a treatment tool such as forceps or an electric scalpel.

The operation section 24 is provided with a freeze switch 24*b*, a mode switching unit 24*c*, a zoom operation unit 24*d* (see FIG. 2), and so forth, in addition to the angle knob 24*a*. The freeze switch 24*b* is capable of performing a freeze operation of displaying a still image of an observation target on the display 21 and a release operation of storing a still image in storage.

In response to the freeze switch 24*b* being operated by a user, a still image of an observation target is freeze-displayed on the display 21. An image storage instruction is output to an image storage control unit 55 or the like, and a still image of the endoscopic image 100 acquired before or after an operation timing of the freeze switch 24*b* is stored in an image storage unit 56 (see FIG. 2) in the processor apparatus 20. The image storage unit 56 is, for example, a storage unit such as a hard disk or a universal serial bus (USB) memory.

The endoscope system 16 has a normal mode, a special-light mode, and an abnormal region detection mode as observation modes. When the observation mode is the normal mode, normal light generated by combining light beams of a plurality of colors at a light amount ratio Lc for the normal mode is emitted. When the observation mode is the special-light mode, special light generated by combining light beams of a plurality of colors at a light amount ratio Ls for the special-light mode is emitted.

When the observation mode is the abnormal region detection mode, illumination light for the abnormal region detection mode is emitted. In the present embodiment, normal light is emitted as the illumination light for the abnormal region detection mode. Alternatively, special light may be emitted.

The processor apparatus 20 is electrically connected to the display 21 and the console 22. The display 21 outputs and displays an image of an observation target, information accompanying the image, and so forth. The console 22 functions as a user interface that receives an input operation of a user.

Figure 2:
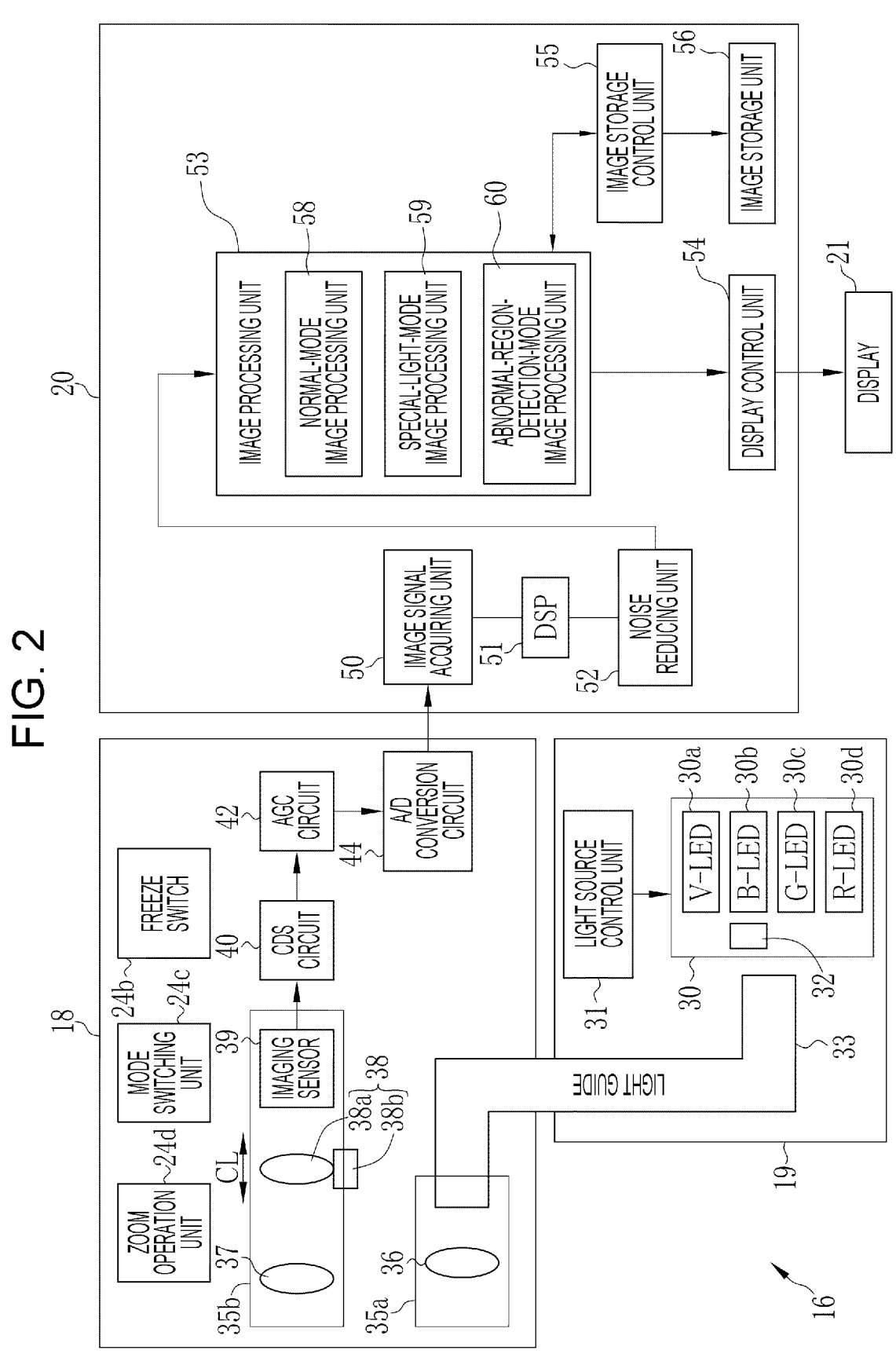
FIG. 2 is a block diagram illustrating the functions of an endoscope system.

As illustrated in FIG. 2, the light source apparatus 19 includes a light source unit 30 that emits illumination light to be used to illuminate an observation target, and a light source control unit 31 that controls the light source unit 30. The light source unit 30 is a semiconductor light source, such as light emitting diodes (LEDs) of a plurality of colors. The light source control unit 31 turns ON/OFF the LEDs or the like and adjusts driving currents and driving voltages for the LEDs or the like, thereby controlling the amount of illumination light to be emitted. In addition, the light source control unit 31 controls the wavelength range of the illumination light by, for example, changing an optical filter.

Figure 3:
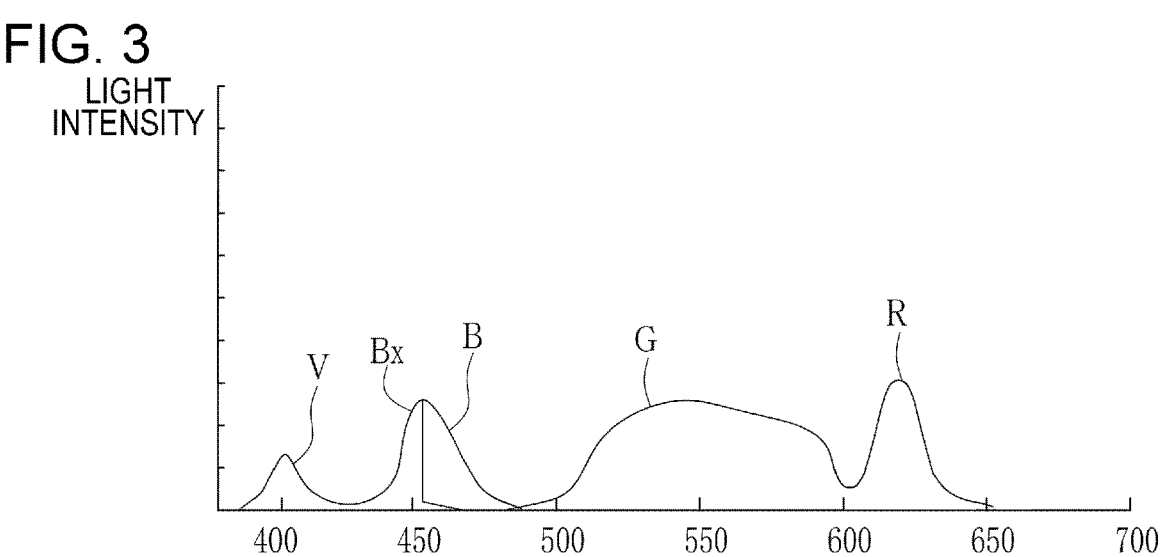
FIG. 3 is a graph illustrating a spectrum of violet light V, blue light B, blue light Bx, green light G, and red light R.

In the first embodiment, the light source unit 30 has LEDs of four colors: a violet light emitting diode (V-LED) 30*a*; a blue light emitting diode (B-LED) 30*b*; a green light emitting diode (G-LED) 30*c*; and a red light emitting diode (R-LED) 30*d*, and a wavelength cut filter 32. As illustrated in FIG. 3, the V-LED 30*a* emits violet light V in a wavelength range of 380 nm to 420 nm.

The B-LED 30*b* emits blue light B in a wavelength range of 420 nm to 500 nm. Of the blue light B emitted by the B-LED 30*b*, at least the longer wavelength side with respect to a peak wavelength of 460 nm is cut off by the wavelength cut filter 32. Accordingly, blue light Bx that has passed through the wavelength cut filter 32 is in a wavelength range of 420 nm to 460 nm. The light in the wavelength range on the longer wavelength side with respect to 460 nm is cut off because the light in the wavelength range on the longer wavelength side with respect to 460 nm is a factor in decreasing the contrast of blood vessels as an observation target. The wavelength cut filter 32 may decrease the amount of light in the wavelength range on the longer wavelength side with respect to 460 nm instead of cutting off the light in the wavelength range on the longer wavelength side with respect to 460 nm.

The G-LED 30c emits green light Gin a wavelength range of 480 nm to 600 nm. The R-LED 30d emits red light R in a wavelength range of 600 nm to 650 nm. The light emitted by each of the LEDs 30a to 30d may have a center wavelength and a peak wavelength that are identical to or different from each other.

The light source control unit 31 controls ON/OFF of each of the LEDs 30a to 30d and the amount of light emission in an ON state independently from each other, thereby adjusting the emission timing, emission period, amount of light, and spectrum of illumination light. The ON/OFF control by the light source control unit 31 varies according to an observation mode. A reference brightness can be set by a brightness setting unit of the light source apparatus 19, the console 22, or the like.

Figure 4:
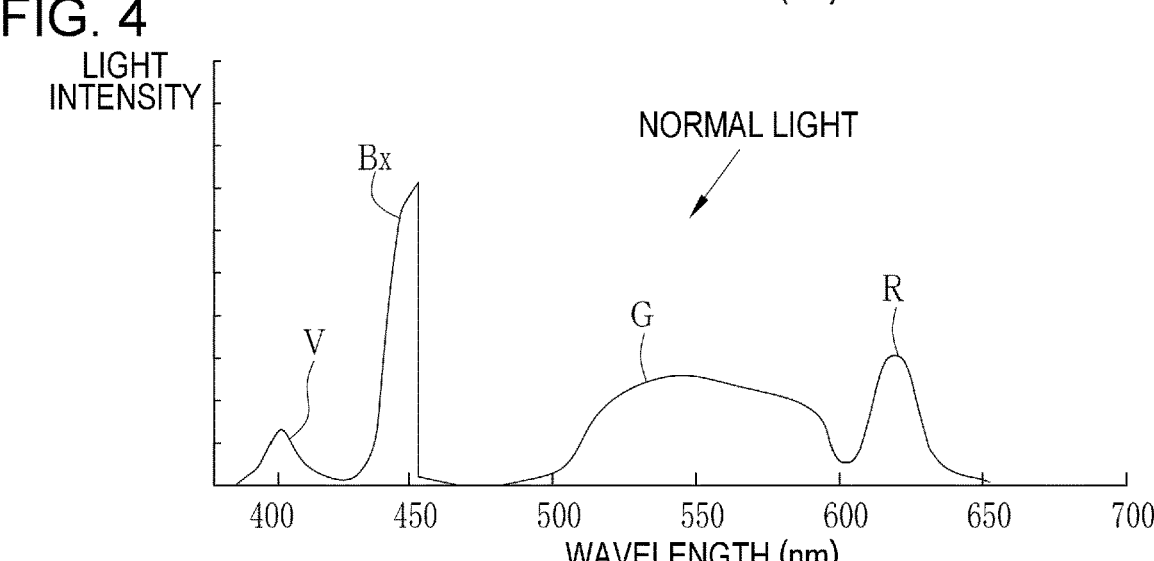
FIG. 4 is a graph illustrating a spectrum of normal light according to a first embodiment.

In the normal mode or the abnormal region detection mode, the light source control unit 31 turns on all of the V-LED 30a, the B-LED 30b, the G-LED 30c, and the R-LED 30d. At this time, as illustrated in FIG. 4, the light amount ratio Lc among the violet light V, the blue light B, the green light G, and the red light R is set such that the peak intensity of the blue light Bx is higher than each of the peak intensities of the violet light V, the green light G, and the red light R. Accordingly, in the normal mode or the abnormal region detection mode, the light source apparatus 19 emits, as normal light, multicolor light for the normal mode or the abnormal region detection mode including the violet light V, the blue light Bx, the green light G, and the red light R. The normal light has a certain intensity or more in the blue range to the red range and is thus substantially white.

Figure 5:
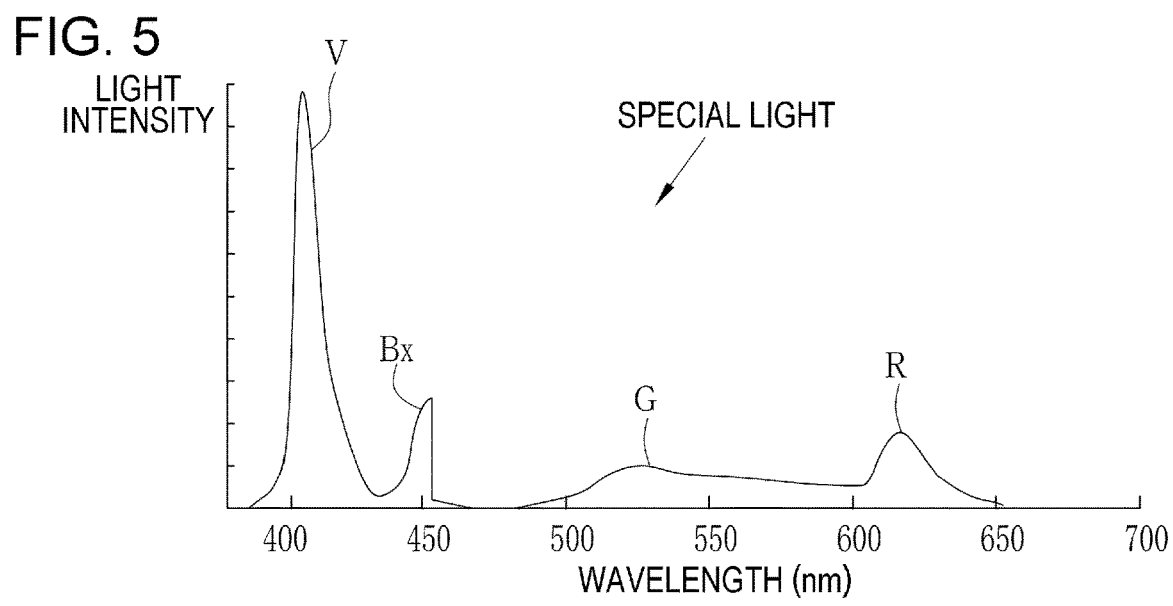
FIG. 5 is a graph illustrating a spectrum of special light according to the first embodiment.

In the special-light mode, the light source control unit 31 turns on all of the V-LED 30a, the B-LED 30b, the G-LED 30c, and the R-LED 30d. At this time, as illustrated in FIG. 5, the light amount ratio Ls among the violet light V, the blue light B, the green light G, and the red light R is set such that the peak intensity of the violet light V is higher than each of the peak intensities of the blue light Bx, the green light G, and the red light R. In addition, the peak intensities of the green light G and the red light R are set so as to be lower than the peak intensities of the violet light V and the blue light Bx. Accordingly, in the special-light mode, the light source apparatus 19 emits, as special light, multicolor light for the special-light mode including the violet light V, the blue light Bx, the green light G, and the red light R. The special light has a large proportion of the violet light V and is thus bluish. The special light does not necessarily need to include light of all the four colors, and may include light from at least one of the LEDs 30a to 30d of four colors. Preferably, the special light may have a main wavelength range, for example, a peak wavelength or a center wavelength, in a range that is 450 nm or less.

As illustrated in FIG. 2, the illumination light emitted by the light source unit 30 passes through a light path coupling unit (not illustrated) formed of a mirror, a lens, and the like and then enters a light guide 33 that extends through the insertion section 23. The light guide 33 is built in the endoscope 18 and a universal cord, and causes the illumination light to propagate to the distal end portion 23a of the endoscope 18. The universal cord is a cord that connects the endoscope 18 to the light source apparatus 19 and the processor apparatus 20. A multimode fiber may be used as the light guide 33. As an example, a small-diameter fiber cable with a core diameter of 105 μm, a clad diameter of 125 μm, and a diameter including a protective layer serving as an outer cover of φ0.3 mm to φ0.5 mm may be used as the light guide 33.

The distal end portion 23a of the endoscope 18 is provided with an illumination optical system 35a and an imaging optical system 35b. The illumination optical system 35a has an illumination lens 36. An observation target is illuminated, via the illumination lens 36, with illumination light that has propagated through the light guide 33. The imaging optical system 35b has an objective lens 37, a magnifying optical system 38, and an imaging sensor 39. Various types of light, such as reflected light, scattered light, and fluorescence from the observation target, enters the imaging sensor 39 through the objective lens 37 and the magnifying optical system 38. Accordingly, an image of the observation target is formed on the imaging sensor 39.

The magnifying optical system 38 includes a zoom lens 38a that magnifies an observation target, and a lens driving unit 38b that moves the zoom lens 38a in optical-axis directions CL. The zoom lens 38a is freely moved between a telephoto end and a wide end in accordance with zoom control by the lens driving unit 38b, thereby magnifying or demagnifying the image of the observation target formed on the imaging sensor 39.

The imaging sensor 39 is a color imaging sensor that performs imaging of an observation target irradiated with illumination light. Each of the pixels of the imaging sensor 39 is provided with a red (R) color filter, a green (G) color filter, or a blue (B) color filter. The imaging sensor 39 receives violet to blue light by using B pixels provided with the B color filter, receives green light by using G pixels provided with the G color filter, and receives red light by using R pixels provided with the R color filter. The imaging sensor 39 outputs image signals of individual colors of RGB from the pixels of the individual colors. The imaging sensor 39 transmits the output image signals to a correlated double sampling (CDS) circuit 40.

In the normal mode or the abnormal region detection mode, the imaging sensor 39 performs imaging of an observation target illuminated with normal light, thereby outputting Bc image signals from the B pixels, outputting Gc image signals from the G pixels, and outputting Rc image signals from the R pixels. In the special-light mode, the imaging sensor 39 performs imaging of an observation target illuminated with special light, thereby outputting Bs image signals from the B pixels, outputting Gs image signals from the G pixels, and outputting Rs image signals from the R pixels.

A charge coupled device (CCD) imaging sensor, a complementary metal-oxide semiconductor (CMOS) imaging sensor, or the like can be used as the imaging sensor 39. Instead of the imaging sensor 39 provided with color filters of the primary colors RGB, a complementary-color imaging sensor including complementary-color filters of cyan (C), magenta (M), yellow (Y), and green (G) may be used. In the case of using the complementary-color imaging sensor, image signals of four colors CMYG are output. Thus, as a result of converting image signals of four colors CMYG into image signals of three colors RGB by using complementary color to primary color conversion, image signals of individual colors RGB similar to those in the imaging sensor 39 can be acquired. Alternatively, a monochrome sensor not provided with color filters may be used instead of the imaging sensor 39.

The imaging sensor 39 captures a moving image to be displayed on the display 21 in real time and captures a still image in response to an operation of the freeze switch 24*b*. For example, capturing of a moving image is started upon the endoscope system 16 being activated.

The CDS circuit 40 performs correlated double sampling (CDS) on analog image signals received from the imaging sensor 39. The image signals output from the CDS circuit 40 are input to an automatic gain control (AGC) circuit 42. The AGC circuit 42 performs automatic gain control (AGC) on the image signals input thereto. An analog to digital (A/D) conversion circuit 44 converts the analog image signals output from the AGC circuit 42 into digital image signals. The A/D conversion circuit 44 inputs the digital image signals generated through the A/D conversion to the processor apparatus 20.

As illustrated in FIG. 2, the processor apparatus 20 includes an image signal acquiring unit 50, a digital signal processor (DSP) 51, a noise reducing unit 52, an image processing unit 53, a display control unit 54, the image storage control unit 55, and the image storage unit 56.

The image processing unit 53 acquires an endoscopic image 100 and detects an abnormal region in an observation target from the endoscopic image 100. The image signal acquiring unit 50 acquires digital image signals based on an observation mode from the endoscope 18. In the normal mode or the abnormal region detection mode, the image signal acquiring unit 50 acquires Bc image signals, Gc image signals, and Rc image signals. In the special-light mode, the image signal acquiring unit 50 acquires Bs image signals, Gs image signals, and Rs image signals. In the abnormal region detection mode, the image signal acquiring unit 50 acquires Bc image signals, Gc image signals, and Rc image signals of one frame during illumination with normal light, and acquires Bs image signals, Gs image signals, and Rs image signals of one frame during illumination with special light.

The DSP 51 performs various signal processing operations, such as defect correction processing, offset processing, DSP gain correction processing, linear matrix processing, gamma conversion processing, and demosaicing processing, on the image signals acquired by the image signal acquiring unit 50. The defect correction processing corrects a signal of a defective pixel of the imaging sensor 39. The offset processing removes a dark current component from the image signal that has been subjected to the defect correction processing and sets an accurate zero level. The DSP gain correction processing multiplies the image signal that has been subjected to the offset processing by a specific DSP gain, thereby adjusting the signal level.

The linear matrix processing increases the color reproducibility of the image signal that has been subjected to the DSP gain correction processing. The gamma conversion processing adjusts the brightness and chroma of the image signal that has been subjected to the linear matrix processing. The image signal that has been subjected to the gamma conversion processing is subjected to demosaicing processing (also referred to as isotropic processing or synchronization processing), thereby generating, through interpolation, a signal of a color insufficient in each pixel. The demosaicing processing enables all the pixels to have signals of individual colors RGB. The noise reducing unit 52 performs noise reduction processing using, for example, a moving-average method, a median filter method, or the like, on the image signal that has been subjected to the demosaicing processing and so forth in the DSP 51, thereby reducing noise. The image signal that has been subjected to the noise reduction is input to the image processing unit 53.

The image processing unit 53 includes a normal-mode image processing unit 58, a special-light-mode image processing unit 59, and an abnormal-region-detection-mode image processing unit 60. The normal-mode image processing unit 58 operates when the normal mode is set, and performs color conversion processing, color enhancement processing, and structure enhancement processing on the Bc image signals, Gc image signals, and Rc image signals that have been received. In the color conversion processing, color conversion processing is performed on the RGB image signals by using 3×3 matrix processing, gradation transformation processing, three-dimensional look up table (LUT) processing, and the like.

The color enhancement processing is performed on the RGB image signals that have been subjected to color conversion processing. The structure enhancement processing is processing of enhancing the structure of an observation target and is performed on the RGB image signals that have been subjected to the color enhancement processing. The above-described various image processing operations enable a normal image to be acquired. The normal image is an image acquired on the basis of normal light including the violet light V, the blue light Bx, the green light G, and the red light R with a well-balanced ratio, and is thus an image with natural colors. The normal image is input to the display control unit 54.

The special-light-mode image processing unit 59 operates when the special-light mode is set. The special-light-mode image processing unit 59 performs color conversion processing, color enhancement processing, and structure enhancement processing on the Bs image signals, Gs image signals, and Rs image signals that have been received. The processing performed in the color conversion processing, the color enhancement processing, and the structure enhancement processing is similar to that performed by the normal-mode image processing unit 58. The above-described various image processing operations enable a special image to be acquired. The special image is an image acquired on the basis of special light in which the amount of the violet light V having a high hemoglobin absorption coefficient of blood vessels is larger than the amount of the blue light Bx, the green light G, and the red light R, and thus the resolution of a blood vessel structure and a gland duct structure is higher than that of other structures. The special image is input to the display control unit 54.

Figure 6:
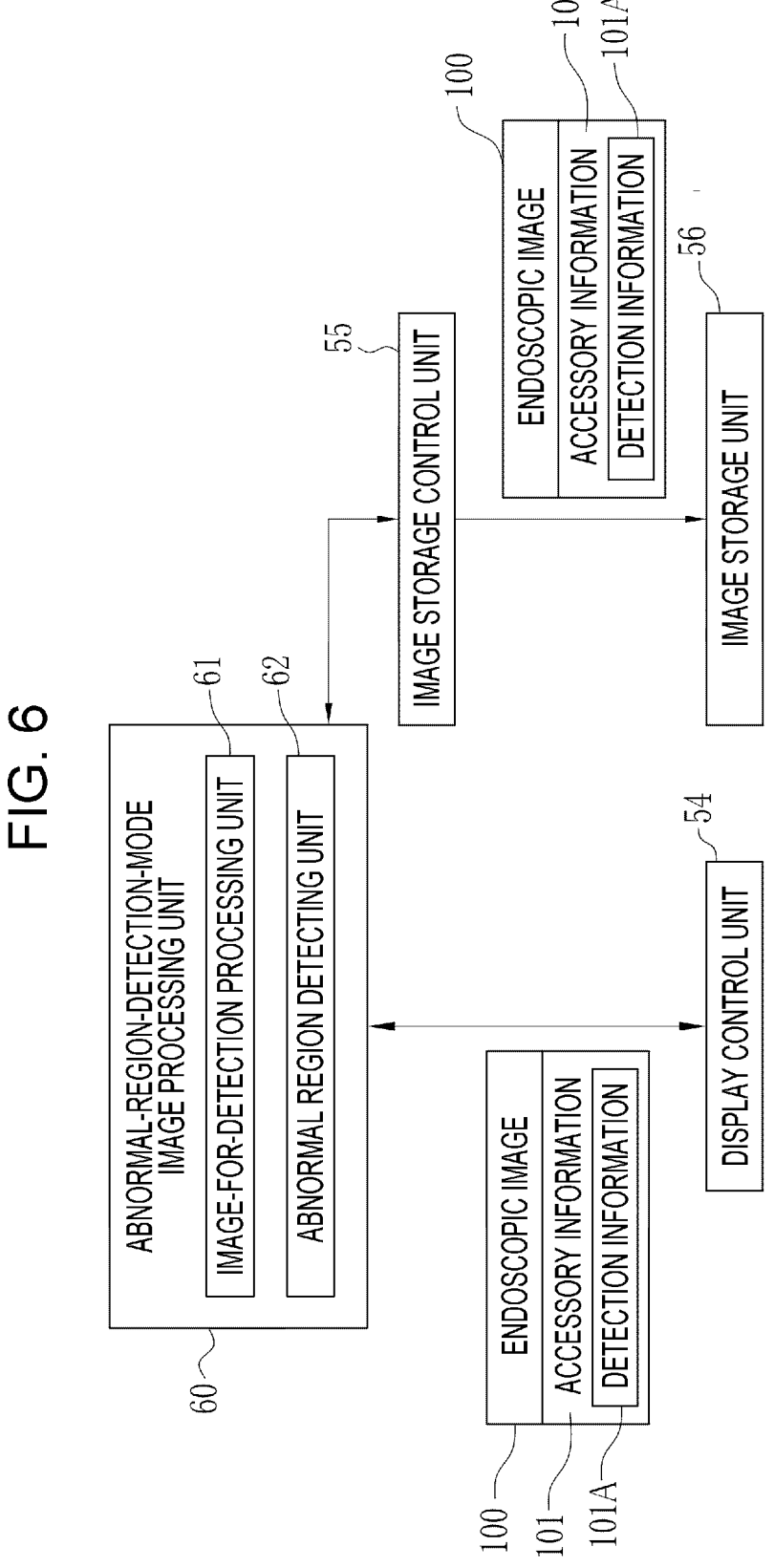
FIG. 6 is a block diagram illustrating the functions of an abnormal-region-detection-mode image processing unit, a display control unit, and an image storage control unit in the endoscope system.

The abnormal-region-detection-mode image processing unit 60 operates when the abnormal region detection mode is set. As illustrated in FIG. 6, the abnormal-region-detection-mode image processing unit 60 has an image-for-detection processing unit 61 and an abnormal region detecting unit 62. The image-for-detection processing unit 61 performs image processing similar to that performed by the normal-mode image processing unit 58, such as color conversion processing, on the Bc image signals, Gc image signals, and Rc image signals that have been received, thereby sequentially acquiring endoscopic images 100.

The abnormal region detecting unit 62 analyzes each endoscopic image 100 and performs abnormal region detection processing for detecting an abnormal region in an observation target. In the present embodiment, the abnormal region detecting unit 62 detects, as an abnormal region, a lesion portion (for example, a tumor, an inflammation, or the like) in the observation target. In this case, the abnormal region detecting unit 62 first divides the endoscopic image 100 into a plurality of small regions, for example, square regions each formed of several pixels. Subsequently, the abnormal region detecting unit 62 calculates image feature quantities from the divided endoscopic image 100. Subsequently, the abnormal region detecting unit 62 recognizes, on the basis of the calculated feature quantities, whether each of the small regions is a lesion portion. Preferably, such recognition processing may be a machine learning algorithm such as a convolutional neural network or deep learning.

Preferably, a feature quantity calculated from the endoscopic image 100 by the abnormal region detecting unit 62 may be the shape or color of a predetermined portion in an observation target, or a value acquired from the shape or color. Preferably, for example, the feature quantity may be at least any one of the density of a blood vessel, the shape of a blood vessel, the number of branches of a blood vessel, the thickness of a blood vessel, the length of a blood vessel, the degree of meandering of a blood vessel, the depth of a blood vessel, the shape of a gland duct, the shape of an opening portion of a gland duct, the length of a gland duct, the degree of meandering of a gland duct, or color information, or the value of a combination of two or more of them.

Finally, the abnormal region detecting unit 62 extracts a group of small regions specified as the same type as one lesion portion. The abnormal region detecting unit 62 records detection information 101A, including information on the position, dimensions, type, and so forth of the extracted lesion portion, as accessory information 101 to accompany the endoscopic image 100.

The display control unit 54 performs display control for displaying an image or data from the image processing unit 53 on the display 21. When the normal mode is set, the display control unit 54 performs control to display a normal image on the display 21. When the special-light mode is set, the display control unit 54 performs control to display a special image on the display 21.

When the abnormal region detection mode is set, the display control unit 54 performs real-time display of emphasizing an abnormal region in the endoscopic image 100, for example, display of emphasizing a lesion portion in the observation target, on the basis of the endoscopic image 100 output from the abnormal-region-detection-mode image processing unit 60 and the detection information 101A recorded as the accessory information 101 in the endoscopic image 100.

At the time of storing the endoscopic image 100, the image storage control unit 55 stores the endoscopic image 100 in the image storage unit 56 with the accessory information 101 including the detection information 101A accompanying the endoscopic image 100. The accessory information 101 recorded in association with each endoscopic image 100 includes a unique image ID, a capturing time, the type of observation mode, and wavelength range information of the light source, in addition to the detection information 101A. The endoscopic image 100 stored in the image storage unit 56 may be an endoscopic image captured as a moving image (frames constituting a moving image) as well as a still image.

As illustrated in FIG. 1, the endoscope system 16 is connected to the endoscopic image viewing support system 10 via the network 14 such as a local area network (LAN) in a hospital. The endoscopic image 100 captured by the endoscope system 16 is stored in the endoscopic image viewing support system 10.

The endoscopic image viewing support system 10 includes the endoscopic image viewing support server 80, a client terminal 81, and a server group 82, which are connected to each other via a network 84 such as a LAN. The endoscopic image viewing support server 80 is a medical image processing apparatus of the present invention that generates and updates the endoscopic image display screen 104 for displaying endoscopic images 100 and distributes the endoscopic image display screen 104 to the client terminal 81 on the basis of a request from the client terminal 81.

The server group 82 is constituted by an image server 86 and a report server 88. The image server 86 includes an image database (hereinafter referred to as an image DB) 90. The image DB 90 stores the endoscopic images 100 transmitted from the endoscope system 16 (see FIG. 7). The report server 88 includes a report database (hereinafter referred to as a report DB) 92. The report DB 92 stores the examination report 94 created in accordance with execution of an endoscopic examination (see FIG. 8). The image DB 90 and the report DB 92 are databases that can be searched using a keyword, such as patient identification data (ID) assigned to each patient or examination ID assigned to each endoscopic examination.

The examination report 94 is a report containing medical findings summarized as a result of viewing the endoscopic images 100 by a doctor such as an examination doctor who has performed an endoscopic examination. The examination report 94 is accompanied by an endoscopic image 100 on which the findings are based.

The client terminal 81 is a terminal for viewing the endoscopic images 100 or the examination report 94, and is used by an examination doctor to view the endoscopic images 100 or create the examination report 94 after an examination has finished. The client terminal 81 is also used by a doctor in a clinical department who has requested an endoscopic examination to view the endoscopic images 100 or the examination report 94. The client terminal 81 is, for example, a notebook or desktop personal computer. In the case of referring to a past examination result, for example, in the case of performing follow-up observation, the doctor uses the client terminal 81 to access the endoscopic image viewing support server 80, and reads out and views the endoscopic images 100 or the examination report 94 stored therein.

Figure 7:
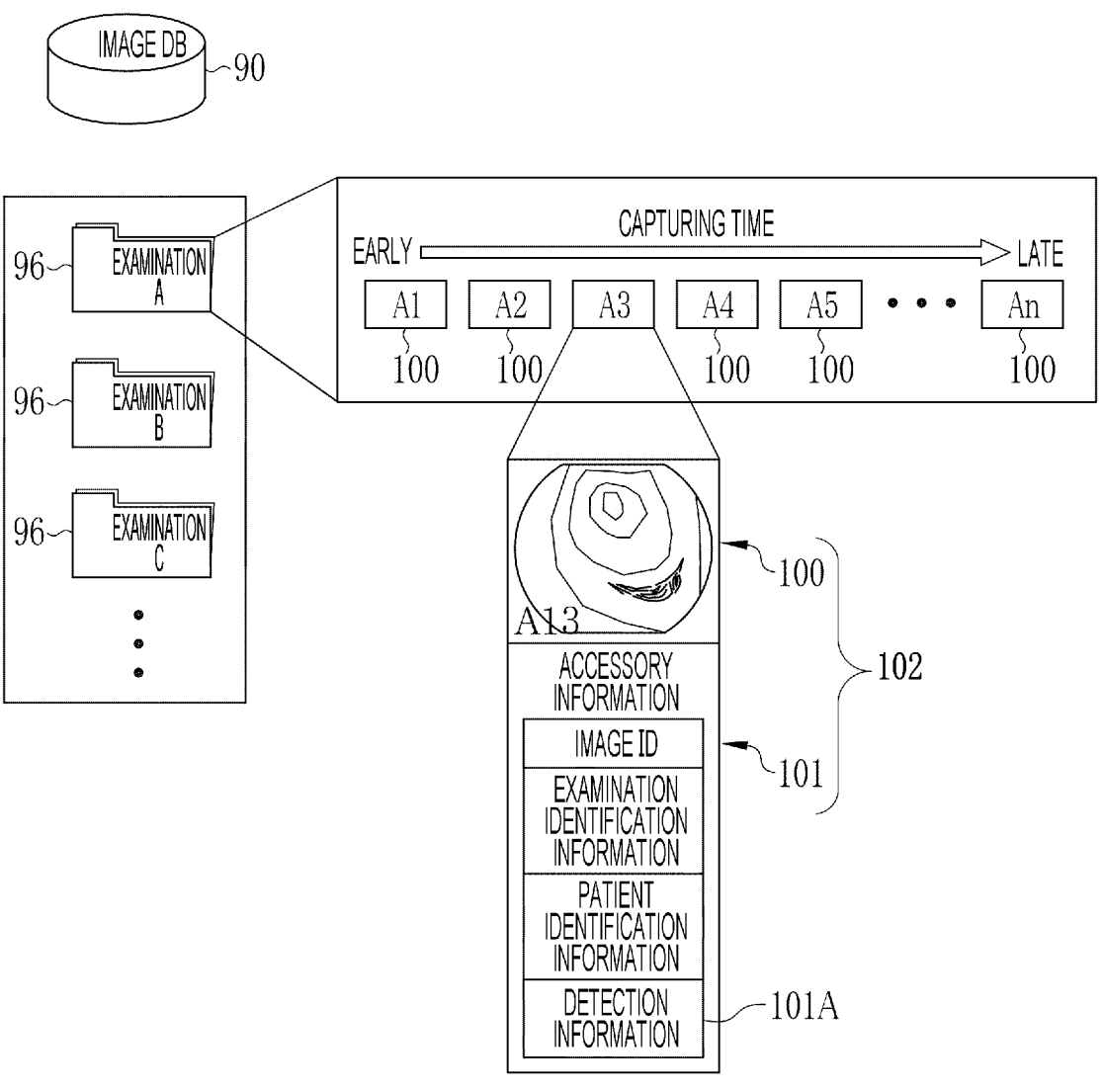
FIG. 7 is an explanatory diagram illustrating the contents of an image DB.

As illustrated in FIG. 7, the image DB 90 is provided with a plurality of image folders 96. Every time an endoscopic examination is performed, one image folder 96 for the endoscopic examination is created. Each image folder 96 stores the endoscopic images 100 acquired in the corresponding endoscopic examination. As described above, in an endoscopic examination, test imaging is performed in addition to capturing of a moving image, capturing of a still image at a certain timing using the freeze switch 24b, and automatic imaging performed at a predetermined time interval, and all the images acquired in these imaging operations are stored as endoscopic images 100 in the image folder 96.

As described above, these endoscopic images 100 are stored, in the image folder 96, as imaging information 102 recorded in association with accessory information 101, such as unique image IDs, capturing times, and detection information. The capturing time recorded as the accessory information 101 for each endoscopic image 100 is used to arrange the endoscopic images 100 in a chronological order when a section-of-interest setting unit 142 described below estimates the degrees of interest of the endoscopic images 100.

FIG. 7 illustrates an example in which n endoscopic images 100 having image IDs A1 to An are stored in the image folder 96 having an examination ID A (examination A). The numbers attached herein as subscripts of A1 to An of the image IDs are attached in ascending order of capturing time. In FIG. 7, the image ID of the endoscopic image 100 having the earliest capturing time is A1, which is followed by A2, A3, . . . An.

The image folder 96 is created in the image server 86 at the time of storing endoscopic images 100 of the unit of examination transmitted from the endoscope system 16. The endoscope system 16 may of course create image folders 96, and the image server 86 may receive each image folder 96. In the image DB 90, no image folders 96 may be provided as long as a plurality of endoscopic images 100 are stored so as to be read out in units of examinations.

Figure 8:
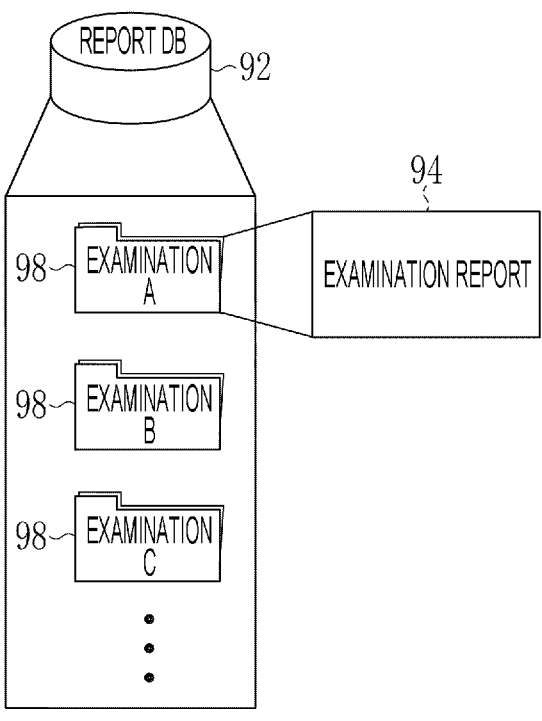
FIG. 8 is an explanatory diagram illustrating the contents of a report DB.

As illustrated in FIG. 8, the report DB 92 is provided with a plurality of report folders 98. The examination report 94 created for each endoscopic examination is stored in the report folder 98. Similarly to the endoscopic images 100, no report folders 98 may of course be provided as long as examination reports 94 are stored so as to be read out in units of endoscopic examinations in the report DB 92.

Figure 9:
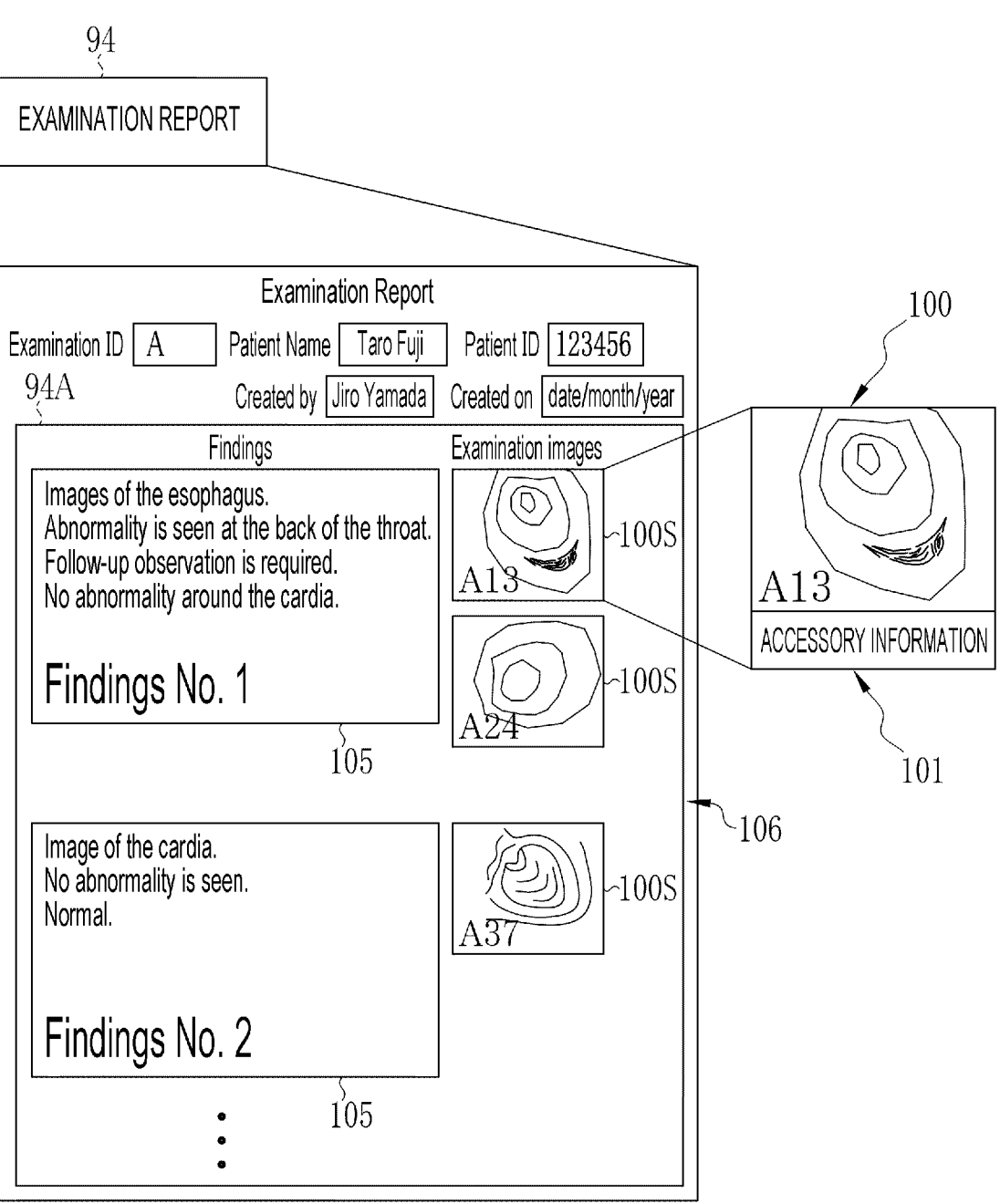
FIG. 9 is an explanatory diagram illustrating the contents of an examination report and a report display screen.

As illustrated in FIG. 9, the examination report 94 and a report display screen 106 for displaying the examination report 94 are constituted by a report main body 94A, the above-described examination identification information and patient identification information, and creator information indicating the creator. The report main body 94A has findings 105 of the examination doctor of the endoscopic examination, and the endoscopic image 100 attached to the examination report 94. The endoscopic image 100 is the endoscopic image 100 serving as the basis of the findings 105, and is attached in association with each findings 105. FIG. 9 illustrates an example in which two endoscopic images 100 having image IDs A13 and A24 are associated with first findings 105 (findings No. 1), and one endoscopic image 100 having an image ID A37 is associated with second findings 105 (findings No. 2).

To create the examination report 94, the endoscopic image viewing support server 80 automatically selects an endoscopic image 100 from among a plurality of endoscopic images 100 acquired in the unit of an endoscopic examination on the basis of the degree of interest of the user described below, attaches the selected endoscopic image 100 in accordance with the format of the examination report 94, and automatically lays out examination identification information, patient identification information, and so forth from the accessory information 101 associated with the endoscopic image 100.

In the following description, the endoscopic images 100 acquired in an endoscopic examination may be distinguishably referred to as: an endoscopic image of interest 100A including an abnormal region; a selected endoscopic image 100S selected on the basis of the degree of interest of the user; and a non-selected endoscopic image 100N not selected on the basis of the degree of interest of the user.

The examination doctor inputs the findings 105 while observing the endoscopic image 100 attached to the examination report 94. When a selected endoscopic image 100S is attached to the examination report 94, for example, the selected endoscopic image 100S is converted into the format of a thumbnail image.

The selected endoscopic image 100S converted into the thumbnail image has the image ID of the original endoscopic image 100 recorded therein as image specification information. The image specification information makes it possible to, when the examination report 94 is read, specify the endoscopic image 100 attached to the examination report 94 from among the plurality of endoscopic images 100 captured in the endoscopic examination on which the examination report 94 is created. FIG. 9 illustrates an example in which three endoscopic images 100 having image IDs A13, A24, and A37 are attached to the examination report 94 of examination A. In FIG. 9 and so forth, symbols such as A13, A24, and A37 attached to the endoscopic images 100 are for the convenience of description, and are not displayed on the actual screen of the endoscopic images 100.

In this example, the selected endoscopic image 100S to be attached to the examination report 94 is converted into a thumbnail format, but the endoscopic image 100 stored in the image folder 96 or a copy thereof may be attached as is without being converted into a thumbnail format. Furthermore, an address or the like of a storage location for accessing the endoscopic image 100 may be recorded in the examination report 94 instead of the endoscopic image 100. The recording of information for accessing the endoscopic image 100 in the examination report 94 is also included in attaching of the endoscopic image 100 to the examination report 94.

The endoscopic image viewing support server 80, the client terminal 81, and the image server 86 and the report server 88 constituting the server group 82 are each configured by installing a control program, such as an operating system, and an application program, such as a client program or a server program, into a computer such as a personal computer, a server computer, or a work station.

Figure 10:
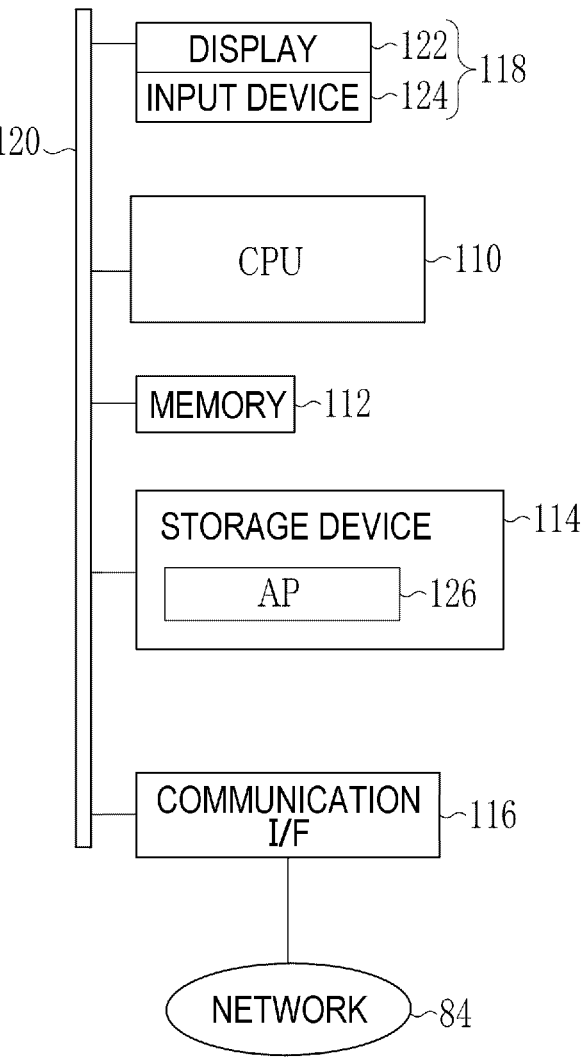

As illustrated in FIG. 10, the computers constituting the individual servers 80, 86, and 88, and the client terminal 81 have the same basic configuration, and each include a central processing unit (CPU) 110, a memory 112, a storage device 114, a communication I/F 116, and an input/output unit 118. These are connected to each other via a data bus 120. The input/output unit 118 is constituted by a display 122 and an input device 124 such as a keyboard and a mouse.

The storage device 114 is, for example, a hard disk drive (HDD), and stores a control program and an application program (hereinafter referred to as an AP) 126. The servers 86 and 88 in which DBs are constructed are provided with, for example, a disk array formed of a plurality of HDDs as the storage device 114 for DB, separately from the HDD storing the programs. The disk array may be built in the server main body, or may be provided separately from the server main body and connected to the server main body through a network such as a LAN.

The memory 112 is a work memory for the CPU 110 to execute processing and is constituted by a random access memory (RAM). The CPU 110 loads the control program stored in the storage device 114 to the memory 112 and executes processing in accordance with the program, thereby centrally controlling individual components of the computer. The communication I/F 116 is a network interface that performs transmission control with respect to the network 84.

The client terminal 81 has a client program installed therein as the AP 126. The client program is a program for causing the client terminal 81 to execute a function of accessing the endoscopic image viewing support server 80 and transmitting various requests such as a viewing request and an update request of the endoscopic image display screen 104 or the report display screen 106, and a function of receiving and displaying the endoscopic image display screen 104 or the report display screen 106 transmitted from the endoscopic image viewing support server 80 to the client terminal 81. The client program may be a program specifically programmed for the endoscopic image viewing support system 10, or may be a well-known web browser.

Figure 11:
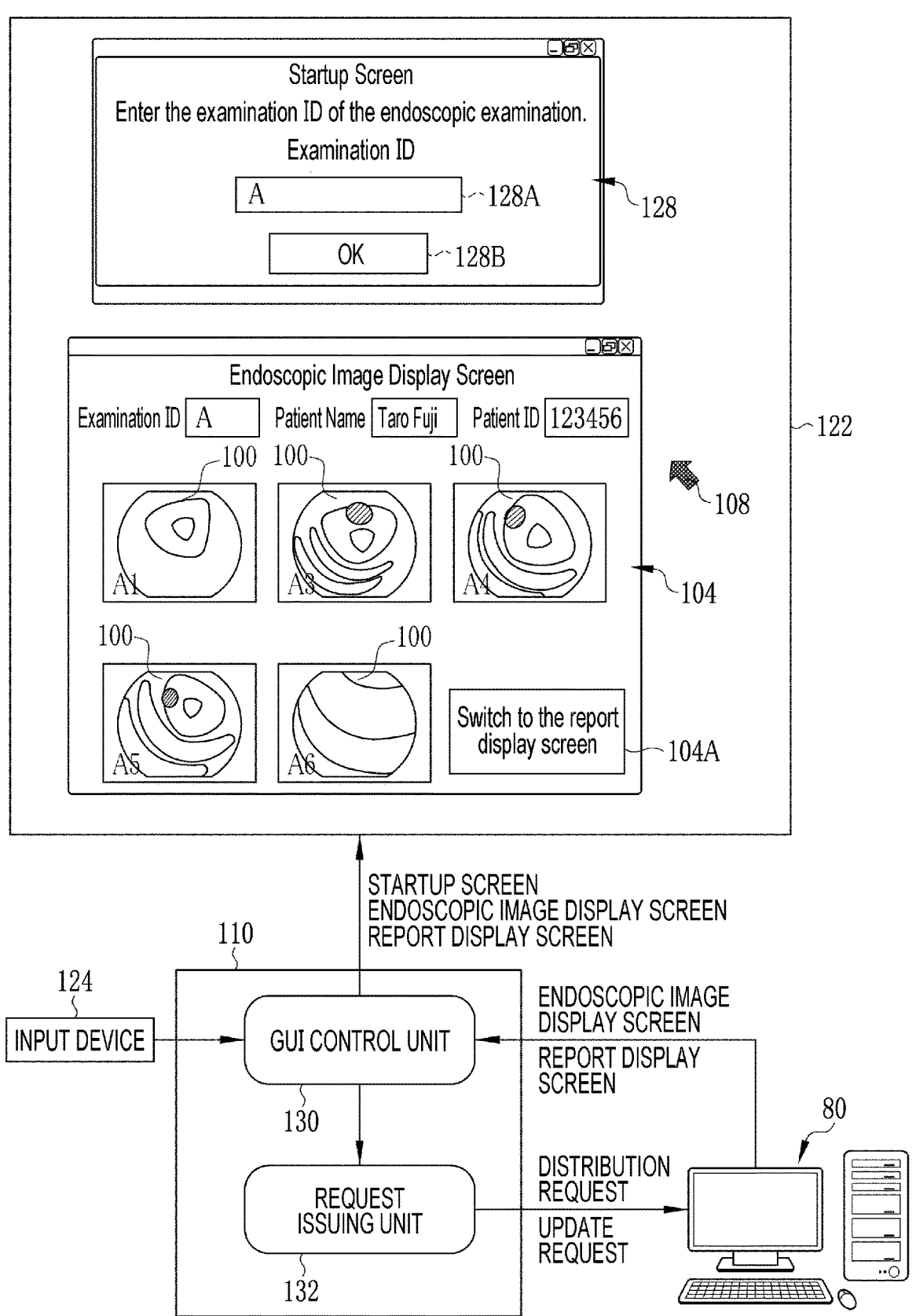
FIG. 11 is an explanatory diagram illustrating an overview of the functions of a client terminal.

As illustrated in FIG. 11, upon the client program being started, a startup screen 128 having an operation function by a graphical user interface (GUI) is displayed on the display 122 of the client terminal 81, and the CPU 110 of the client terminal 81 functions as a GUI control unit 130 and a request issuing unit 132 that issues various requests to the endoscopic image viewing support server 80 in cooperation with the memory 112 and so forth.

The startup screen 128 is provided with an examination ID input field 128A and an OK button 128B. Inputting of an examination ID in the examination ID input field 128A and operating of the OK button 128B make it possible to designate one endoscopic examination from among a plurality of endoscopic examinations. Upon an endoscopic examination being designated, the information input to the examination ID input field 128A is transmitted from the GUI control unit 130 to the request issuing unit 132. The request issuing unit 132 generates a distribution request for the endoscopic image display screen 104 for displaying the endoscopic images 100 acquired in the designated endoscopic examination, that is, the endoscopic examination corresponding to the examination ID input to the examination ID input field 128A, and issues the distribution request to the endoscopic image viewing support server 80. In response to the distribution request, the endoscopic image display screen 104 in an initial state is distributed by the endoscopic image viewing support server 80 and displayed on the display 122 of the client terminal 81.

The endoscopic image display screen 104 is composed of data described in a markup language such as an extensible markup language (XML), and the endoscopic image display screen 104 itself has an operation function by a GUI. The GUI control unit 130 receives operation instructions from the input device 124 through the endoscopic image display screen 104, such as an input operation from a keyboard and a click operation of an operation button by a pointer 108 of a mouse. The request issuing unit 132 issues, for example, an update request of the endoscopic image display screen 104 in response to an operation instruction received by the GUI control unit 130.

The update request includes an instruction to update the display contents of the endoscopic image display screen 104, such as an instruction to switch the endoscopic image 100 to be displayed or an instruction to switch the display mode. Upon the update request being transmitted to the endoscopic image viewing support server 80, the endoscopic image viewing support server 80 updates the endoscopic image display screen 104 and distributes the updated endoscopic image display screen 104 to the client terminal 81. Accordingly, the endoscopic image display screen 104 displayed on the client terminal 81 is updated.

On the endoscopic image display screen 104, a plurality of endoscopic images 100 selected by an endoscopic image selecting unit 143 described below are displayed. In addition, an examination ID of an endoscopic examination, and a patient name and a patient ID of an examination target of the endoscopic examination are displayed.

Configuration of Medical Image Processing Apparatus

Figure 12:
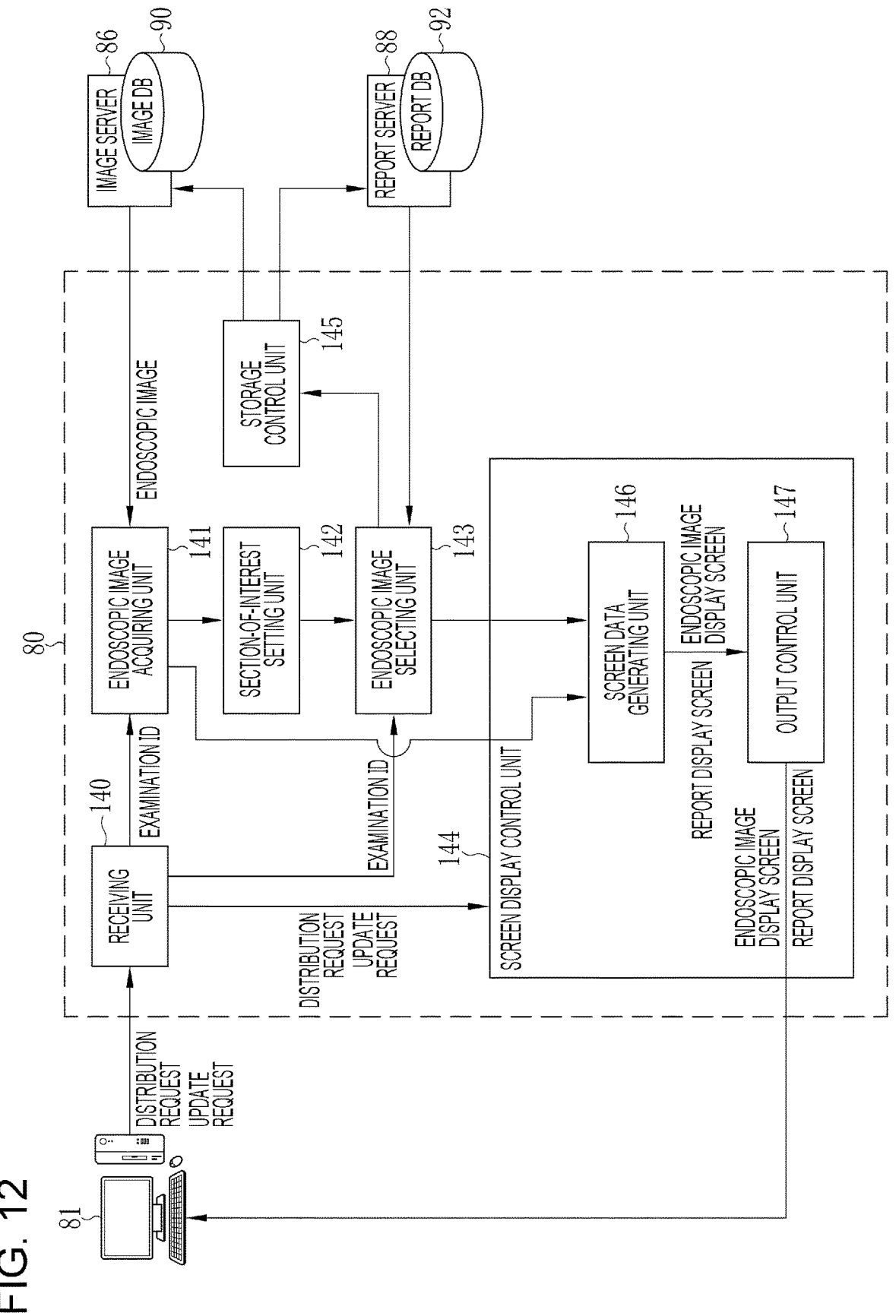
FIG. 12 is an explanatory diagram illustrating an overview of the functions of the endoscopic image viewing support server.

As illustrated in FIG. 12, the endoscopic image viewing support server 80 has a server program installed therein as the AP 126. The server program is an operation program for causing a computer to function as the endoscopic image viewing support server 80 (a medical image processing apparatus). Upon the server program being started, the CPU 110 of the endoscopic image viewing support server 80 cooperates with the memory 112 and so forth to function as a receiving unit 140, an endoscopic image acquiring unit 141

(corresponding to an imaging information acquiring unit), the section-of-interest setting unit 142, the endoscopic image selecting unit 143 (corresponding to a medical image selecting unit), a screen display control unit 144, and a storage control unit 145.

The receiving unit 140 receives a distribution request and an update request for the endoscopic image display screen 104 or the report display screen 106 input from the client terminal 81, and outputs these requests to the screen display control unit 144. As described above, a distribution request for the endoscopic image display screen 104 is a request for distributing the endoscopic image display screen 104 that displays an endoscopic image 100 selected from among a plurality of endoscopic images 100 designated by an examination ID input to the examination ID input field 128A of the startup screen 128. Upon receiving the distribution request, the receiving unit 140 inputs the examination ID designated in the distribution request (the examination ID input to the examination ID input field 128A) to the endoscopic image acquiring unit 141 and the endoscopic image selecting unit 143.

Figure 13:
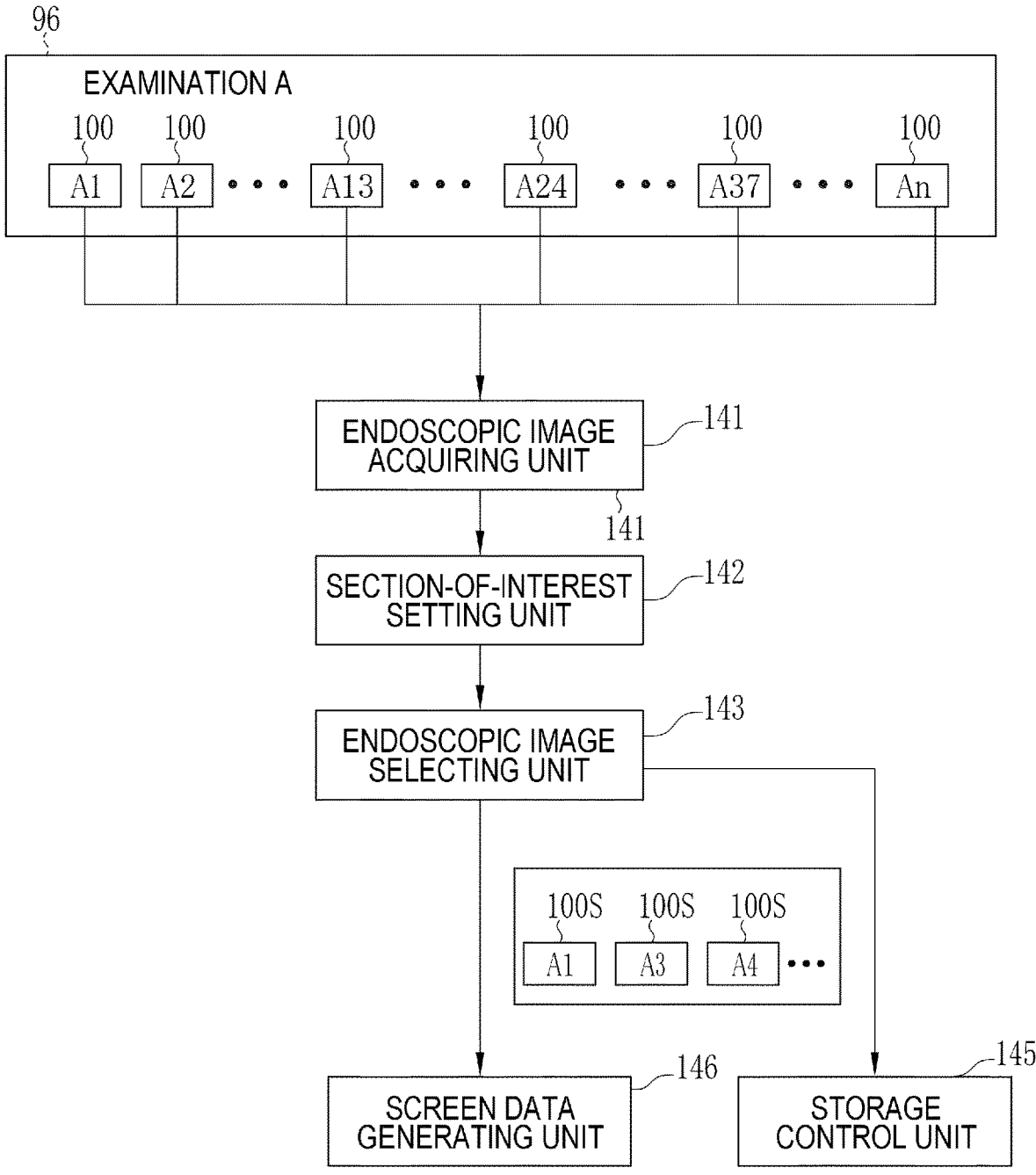
FIG. 13 is an explanatory diagram illustrating an overview of processing in an endoscopic image acquiring unit, a section-of-interest setting unit, and an endoscopic image selecting unit.

As illustrated in FIG. 13, upon the examination ID being input, the endoscopic image acquiring unit 141 accesses the image server 86 and acquires from the image DB 90 all the endoscopic images 100 acquired in the endoscopic examination corresponding to the notified examination ID. Specifically, the endoscopic image acquiring unit 141 searches the image DB 90 by using the examination ID as a search keyword, and reads out and acquires imaging information 102 having the common examination ID from an image folder 96 of the image DB 90. As described above, the imaging information 102 includes endoscopic images 100 and accessory information 101 recorded in association with the endoscopic images 100. Accordingly, all of the plurality of endoscopic images 100 of the unit of examination acquired in one endoscopic examination and the accessory information 101 recorded in association with the endoscopic images 100 are acquired. The endoscopic image acquiring unit 141 outputs the acquired endoscopic images 100 and accessory information 101 to the section-of-interest setting unit 142 and the endoscopic image selecting unit 143.

The section-of-interest setting unit 142 estimates, from the endoscopic images 100 or the accessory information 101, the degree of interest of the user when the endoscopic images 100 are captured (hereinafter simply referred to as the degree of interest). In the present embodiment, the degree of interest is estimated from the detection information 101A included in the accessory information 101. As for an endoscopic image 100 satisfying a predetermined condition, the degree of interest is estimated by using image processing. After estimating the degree of interest when the endoscopic images 100 are captured, the section-of-interest setting unit 142 sets, in accordance with the degree of interest of each endoscopic image 100, sections of interest to which the endoscopic images 100 are classified. The estimation of the degree of interest and the setting of the sections of interest performed by the section-of-interest setting unit 142 will be described in detail below.

The endoscopic image selecting unit 143 selects an endoscopic image 100 from each section of interest set by the section-of-interest setting unit 142 at a ratio based on the degree of interest estimated by the section-of-interest setting unit 142. That is, the endoscopic image selecting unit 143 selects a large number of endoscopic images 100 from a section of interest having a high degree of interest, and selects a small number of endoscopic images 100 from a section of interest having a low degree of interest. The endoscopic image selecting unit 143 outputs the endoscopic images 100 selected in the above-described manner as selected endoscopic images 100S to the storage control unit 145 and a screen data generating unit 146.

The screen display control unit 144 has the screen data generating unit 146 and an output control unit 147. The screen data generating unit 146 receives the endoscopic images 100 directly from the endoscopic image acquiring unit 141, and the selected endoscopic images 100S from the endoscopic image selecting unit 143.

The screen data generating unit 146 generates and updates the endoscopic image display screen 104, which displays the input selected endoscopic images 100S or the endoscopic images 100 including the selected endoscopic images 100S, or the report display screen 106. The image data generating unit 146 generates the endoscopic image display screen 104 or the report display screen 106 by using the selected endoscopic images 100S and the accessory information 101 recorded in association with these selected endoscopic images 100S.

The generated and updated endoscopic image display screen 104 is input to the output control unit 147. The output control unit 147 distributes the endoscopic image display screen 104 or the report display screen 106 input thereto to the client terminal 81 as a request source. In the client terminal 81, the endoscopic image display screen 104 distributed from the output control unit 147 is displayed on the display 122.

The display mode of the endoscopic image display screen 104 has at least a selected endoscopic image display mode (the display mode illustrated in FIG. 11) in which selected endoscopic images 100S are extracted from a plurality of endoscopic images 100 acquired in the unit of examination and only the selected endoscopic images 100S are displayed in a chronological order.

In the present embodiment, the endoscopic image display screen 104 is provided with a switch button 104A for switching to the report display screen 106. For example, selecting of one of the selected endoscopic images 100S displayed on the endoscopic image display screen 104 and selecting of the switch button 104A enable switching to the report display screen 106 that displays the examination report 94 accompanied by the selected endoscopic images 100S.

The storage control unit 145 performs control to store the selected endoscopic images 100S in a storage device. In the present embodiment, the storage control unit 145 transmits the selected endoscopic images 100S to the image server 86 and causes the image DB 90 to store the selected endoscopic images 100S. In this case, information indicating the selected endoscopic images 100S may be recorded in the accessory information 101 of the endoscopic images 100 already stored in the image server 86 and having the same image ID, instead of newly storing the selected endoscopic images 100S. The storage location of the selected endoscopic images 100S stored by the storage control unit 145 is not limited to the image DB 90. The selected endoscopic images 100S may be attached to the examination report 94, transmitted to the report server 88, and stored in the report DB 92, or may be stored in a storage device provided in the endoscopic image viewing support server 80.

Figure 14:
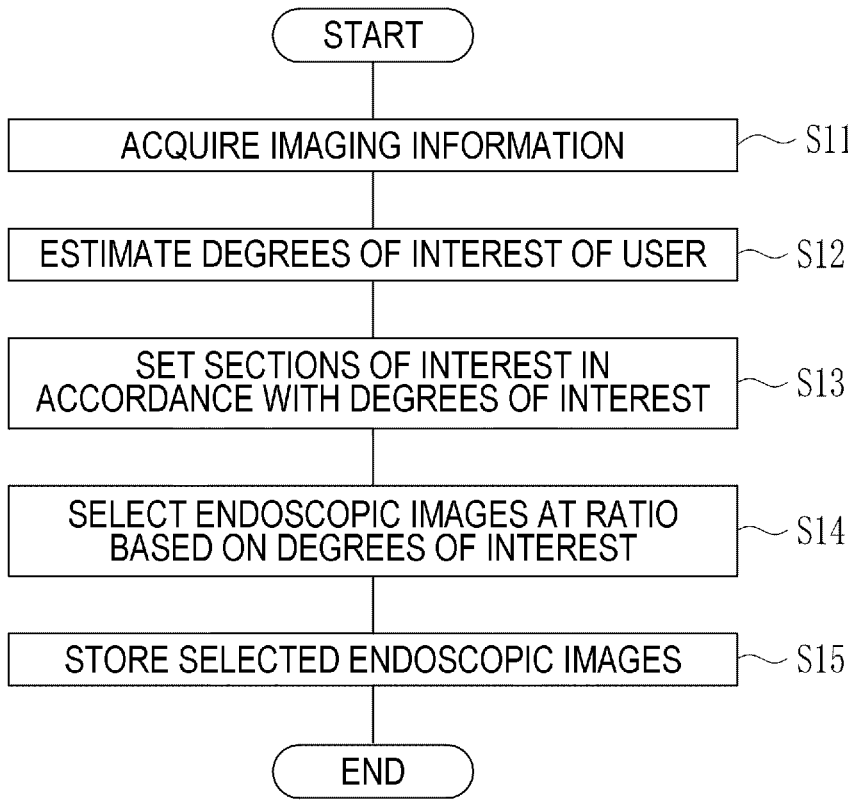
FIG. 14 is a flowchart illustrating a processing procedure of the present invention.

With reference to the flowchart illustrated in FIG. 14 and the explanatory diagrams illustrated in FIG. 15 and FIG. 16, a more detailed description will be given of acquisition of endoscopic images 100, estimation of the degree of interest, selection and storage of endoscopic images, and so forth in the endoscopic image viewing support server 80. First, in response to receipt of a distribution request from the client terminal 81 as described above, the endoscopic image acquiring unit 141 searches the image DB 90, and reads out and acquires imaging information 102 of the unit of examination acquired in one endoscopic examination, that is, a plurality of endoscopic images 100 and accessory information 101 recorded in association with the endoscopic images 100, from the image DB 90 (S11).

Subsequently, for the plurality of endoscopic images 100 of the unit of examination and the accessory information 101 recorded in association with the endoscopic images 100 that have been acquired, the section-of-interest setting unit 142 estimates the degrees of interest from the detection information 101A included in the accessory information 101 (S12). In the case of estimating the degrees of interest from the detection information 101A, the estimation is performed by determining whether there is an abnormal region in each endoscopic image 100 from the detection information 101A, as illustrated in part (A) of FIG. 15. That is, for the endoscopic images 100 having image IDs A1, A2, and A6 and having no abnormal region, it is estimated that the degree of interest is the lowest. FIG. 15 and FIG. 16 illustrate a case in which 1 is the lowest and 10 is the highest as the value of the degree of interest. Part (A) of FIG. 15 illustrates an example in which a plurality of endoscopic images 100 of the unit of examination acquired in one endoscopic examination are arranged in a chronological order, in which the endoscopic images 100 having an image ID A7 or thereafter are omitted for the convenience of illustration.

On the other hand, for the endoscopic images 100 having image IDs A3 to A5 and having a lesion portion LS which is an abnormal region, the section-of-interest setting unit 142 estimates that the degree of interest is high, and determines that these endoscopic images 100 having the abnormal region are endoscopic images of interest 100A (corresponding to medical images of interest).

Subsequently, as illustrated in part (B) of FIG. 15, in a case where the plurality of endoscopic images 100 are arranged in a chronological order, the section-of-interest setting unit 142 estimates the degree of interest for at least one endoscopic image 100 in an endoscopic image group (corresponding to a medical image group) composed of the endoscopic images 100 having image IDs A3 to A5 and including the endoscopic image of interest 100A by using image processing. In the example illustrated in part (B) of FIG. 15, the degree of interest is estimated, by using image processing, for the endoscopic image of interest 100A having an image ID A4 and chronologically located at the center among the endoscopic images of interest 100A having image IDs A3 to A5 and satisfying a condition in the endoscopic image group described above.

In the estimation of the degree of interest using image processing, the section-of-interest setting unit 142 uses, as the degree of interest, the degree of similarity between the endoscopic image of interest 100A having an image ID A4 as an estimation target of the degree of interest, and the preceding and subsequent endoscopic images 100 having image IDs A3 and A5 in an arrangement in a chronological order. The degree of similarity can be calculated by well-known pattern matching. The calculation of the degree of similarity is not limited thereto, and any method capable of calculating the degree of similarity may be used, such as a method of comparing average colors of the endoscopic images 100, a method of comparing feature quantities, such as the positions or areas of abnormal regions, or a method using a neural network.

Figure 15:
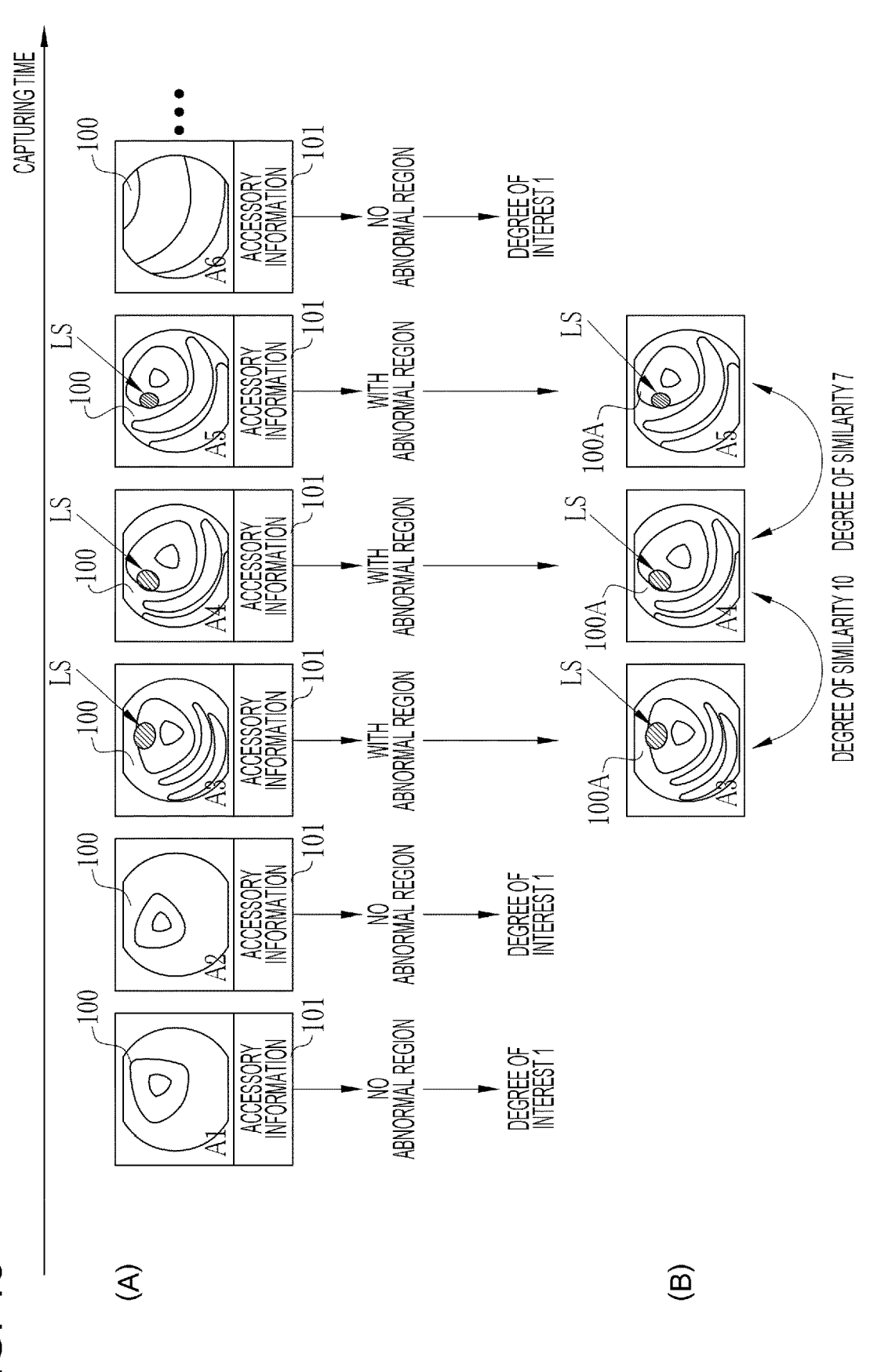
FIG. 15 is an explanatory diagram of estimating the degrees of interest from a plurality of medical images in the present invention.

In the example illustrated in part (B) of FIG. 15, the endoscopic image of interest 100A having an image ID A4 has a degree of similarity of 10 with respect to the endoscopic image 100 having an image ID A3, and has a degree of similarity of 7 with respect to the endoscopic image 100 having an image ID A5. As described above, the section-of-interest setting unit 142 uses the degrees of similarity as the degree of interest for the endoscopic image of interest 100A having an image ID A4. In this case, the degrees of similarity with respect to the preceding and subsequent endoscopic images 100 having image IDs A3 and A5 are values different from each other, and the degree of similarity having a larger value is used as the degree of interest. Alternatively, an average value of the degrees of similarity with respect to the preceding and subsequent endoscopic images 100 may be used as the degree of interest. In the present embodiment, the degrees of similarity are obtained in a similar manner for the endoscopic images of interest 100A having image IDs A3 and A5.

Figure 16:
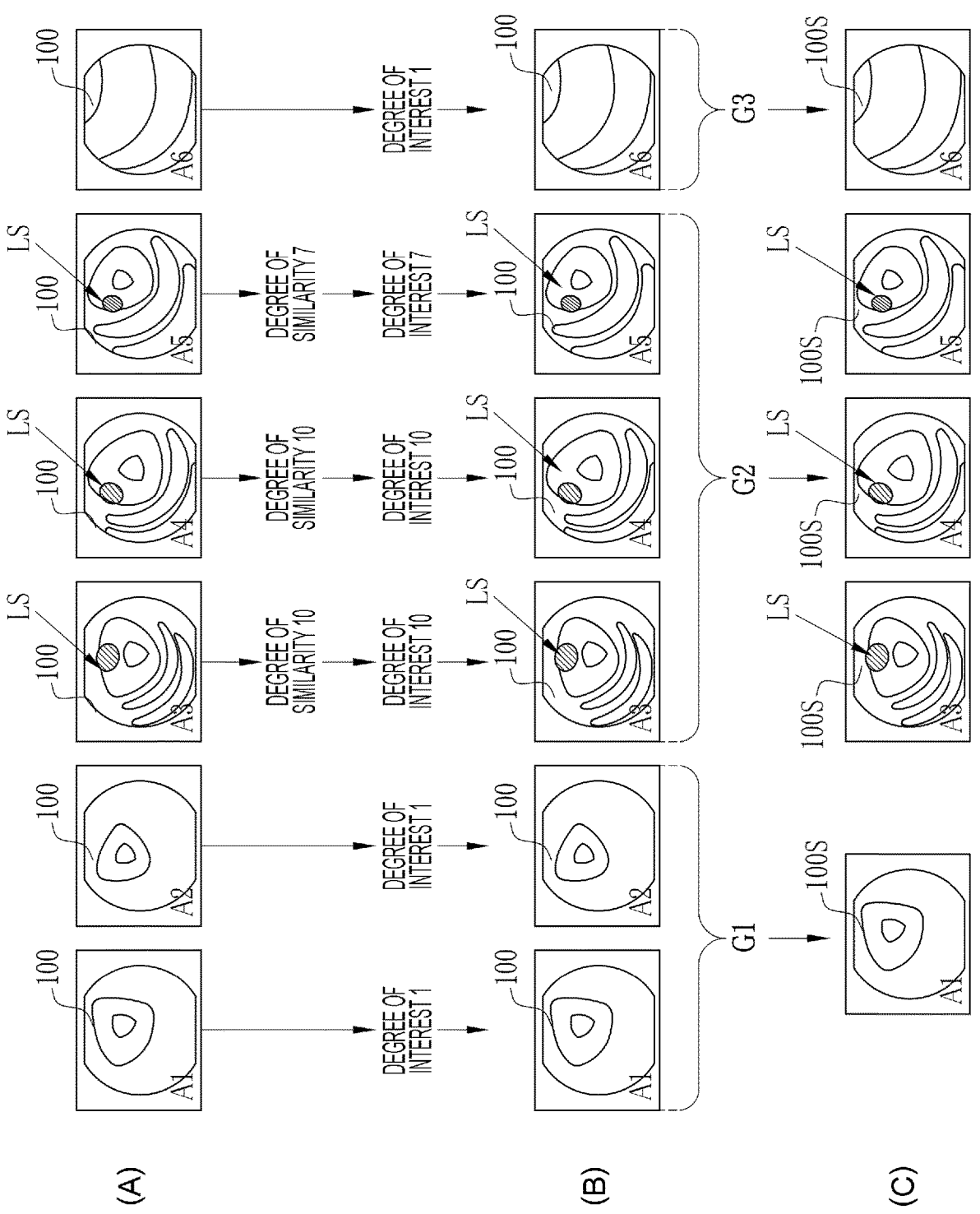
FIG. 16 is an explanatory diagram of selecting medical images at a ratio based on the degrees of interest in the present invention.

As illustrated in part (A) of FIG. 16, the degrees of similarity are calculated in the above manner for the endoscopic images 100 having image IDs A3, A4, and A5. The degrees of similarity are 10, 10, and 7, respectively. That is, the degrees of interest for the endoscopic images 100 having image IDs A3, A4, and A5 estimated by the section-of-interest setting unit 142 are 10, 10, and 7, respectively.

Subsequently, the section-of-interest setting unit 142 sets sections of interest to which the plurality of endoscopic images 100 are classified in accordance with the calculated degrees of interest (S13). In the example illustrated in part (B) of FIG. 16, the endoscopic images 100 having image IDs A1 and A2 are classified into a section of interest G1, the endoscopic images 100 having image IDs A3 to A5 are classified into a section of interest G2, and the endoscopic image 100 having an image ID A6 is classified into a section of interest G3, in accordance with the degrees of interest. In the classification according to the degrees of interest by the section-of-interest setting unit 142, for example, the degrees of interest of the endoscopic images 100 chronologically adjacent to each other are compared with each other. If the difference is smaller than a certain threshold value, the endoscopic images 100 belong to the same section of interest. If the difference is greater than or equal to the threshold value, the endoscopic images 100 belong to different sections of interest. In this way, the section-of-interest setting unit 142 sets sections of interest by repeating comparison of the degrees of interest of the endoscopic images 100 chronologically adjacent to each other. The section-of-interest setting unit 142 outputs the set sections of interest and the degrees of interest of the individual endoscopic images to the endoscopic image selecting unit 143.

Subsequently, the endoscopic image selecting unit 143 selects an endoscopic image 100 from each of the sections of interest G1 to G3 at a ratio corresponding to the degrees of interest (S14). In this case, for example, an average value of the degrees of interest of the endoscopic images 100 is calculated in each of the sections of interest G1 to G3. The average value of the degree of interest is 1 in the sections of interest G1 and G3, and the average value of the degree of interest is 9 in the section of interest G2. Alternatively, the largest value of the degree of interest in each of the sections of interest G1 to G3 may be used.

As described above, the endoscopic image selecting unit 143 determines a ratio from the degrees of interest in each of the sections of interest G1 to G3, and selects endoscopic images 100 at the ratio. In the example illustrated in FIG. 15, the ratio is 1:9:1.

In the example illustrated in part (C) of FIG. 16, the number of selected endoscopic images 100S selected from the sections of interest G1 and G3 having a low degree of interest is one, which is the number based on the lowest ratio. On the other hand, the number of selected endoscopic images 100S selected from the section of interest G2 having a high degree of interest is three, which is the number based on the highest ratio. If the number of images based on the ratio is smaller than 1, the number is rounded up to 1. Alternatively, if the number of images based on the ratio is smaller than 1, the number may be rounded down to 0.

In the example illustrated in part (C) of FIG. 16, all the selected endoscopic images 100S are selected as a result based on the ratio from the section of interest G2 having a high degree of interest. If the number of images based on the ratio is smaller than the number of endoscopic images 100 belonging to the section of interest, for example, the endoscopic images may be selected in descending order of the degree of interest in the section of interest.

The selected endoscopic images 100S selected from the individual sections of interest at the ratio based on the degrees of interest are output to the screen display control unit 144 and the storage control unit 145. The storage control unit 145 causes the image DB 90 to store the selected endoscopic images 100S (S15). On the other hand, the selected endoscopic images 100S input to the screen display control unit 144 are used to generate the endoscopic image display screen 104 or the report display screen 106.

As described above, in the endoscopic image viewing support server 80, the degrees of interest are estimated from the accessory information 101 recorded in association with the endoscopic images 100, the degrees of interest are estimated from the endoscopic images 100 by using image processing, and sections of interest classified in accordance with the degrees of interest are set. Accordingly, the degree of interest of the user can be estimated more accurately, and the ratio of the selected endoscopic images 100S based on the degree of interest becomes appropriate. This makes it possible to select an endoscopic image reflecting the policy of a doctor or a hospital from a plurality of endoscopic images with high accuracy and at an appropriate ratio, and reduce the burden on the doctor.

Second Embodiment

Figure 17:
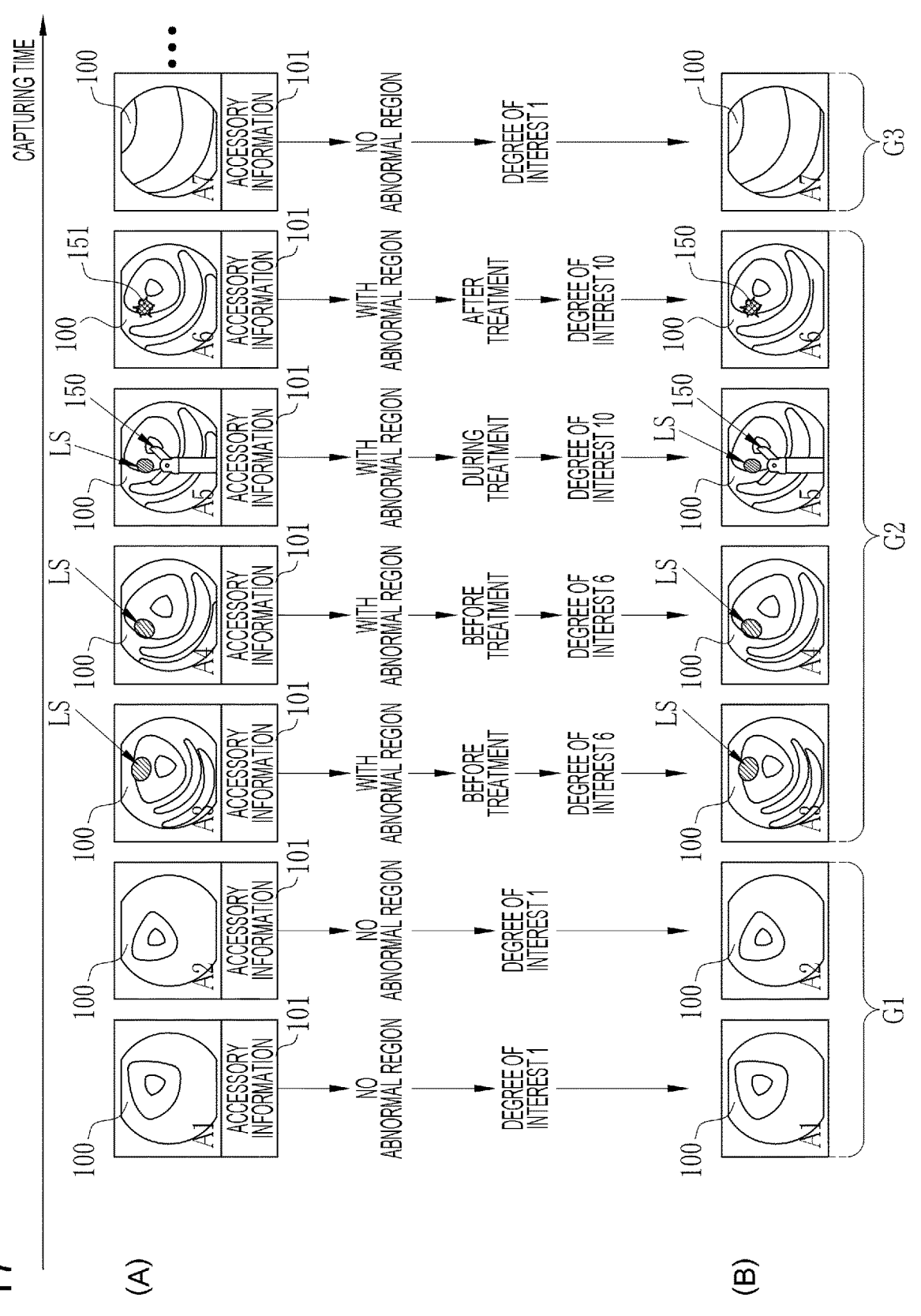
FIG. 17 is an explanatory diagram of estimating the degrees of interest from a plurality of medical images in a second embodiment.

In the above-described first embodiment, the degrees of similarity between a medical image of interest and the preceding and subsequent endoscopic images are used as the degree of interest of the user estimated by the section-of-interest setting unit 142. Alternatively, a state of treatment for an abnormal region may be used as the degree of interest to be estimated. In FIG. 17, treatment is given to a lesion portion LS as an abnormal region by using a treatment tool 150 in an endoscopic examination, and detection information on the detected abnormal region and treatment state information of the treatment tool 150 are recorded in the accessory information 101. The second embodiment is similar to the above-described first embodiment except that a state of treatment for an abnormal region is used as the degree of interest to be estimated, and the description will be omitted.

First, in response to receipt of a distribution request from the client terminal 81, the endoscopic image acquiring unit 141 reads out and acquires a plurality of endoscopic images 100 acquired in one endoscopic examination, and accessory information 101 recorded in association with the endoscopic images 100, from the image DB 90 as in the above-described first embodiment.

Subsequently, as illustrated in part (A) of FIG. 17, the section-of-interest setting unit 142 estimates the degrees of interest from the accessory information 101. In the present embodiment, the state of treatment with the treatment tool 150 is determined together with the presence or absence of an abnormal region in each endoscopic image 100. That is, for the endoscopic images 100 having image IDs A1, A2, and A7 and having no abnormal region, it is estimated that the degree of interest is 1, which is the lowest. Part (A) of FIG. 17 illustrates an example in which a plurality of endoscopic images 100 of the unit of examination acquired in one endoscopic examination are arranged in a chronological order, in which the endoscopic images 100 having an image ID A8 or thereafter are omitted for the convenience of illustration.

On the other hand, for the endoscopic images 100 having image IDs A3 to A6 and having a lesion portion LS which is an abnormal region, the section-of-interest setting unit 142 estimates that the degree of interest is high, and determines the treatment state for these endoscopic images 100 having the abnormal region. In this case, the endoscopic image 100 including a resection scar 151 of the lesion portion LS resected with the treatment tool 150 (the endoscopic image 100 having an image ID A6 in part (A) of FIG. 17) is also included in the endoscopic images 100 having an abnormal region. The degree of interest is 6 for the endoscopic images 100 having image IDs A3 and A4, having an abnormal region, and showing a treatment state which is before treatment. The degree of interest is 10, which is the highest, for the endoscopic images 100 having image IDs A5 and A6 and showing treatment states which are during treatment and after treatment.

Subsequently, the section-of-interest setting unit 142 sets sections of interest to which the plurality of endoscopic images 100 are classified in accordance with the calculated degrees of interest. In the example illustrated in part (B) of FIG. 17, the endoscopic images 100 having image IDs A1 and A2 are classified into a section of interest G1, the endoscopic images 100 having image IDs A3 to A6 are classified into a section of interest G2, and the endoscopic image 100 having an image ID A7 is classified into a section of interest G3, in accordance with the degrees of interest. The classification according to the degrees of interest by the section-of-interest setting unit 142 is similar to that in the above-described first embodiment. The section-of-interest setting unit 142 outputs the set sections of interest and the degrees of interest of the individual endoscopic images to the endoscopic image selecting unit 143.

As described above, by using a state of treatment for an abnormal region as the degree of interest to be estimated, the degree of interest of the user can be estimated more accurately, and the ratio of the selected endoscopic images 100S based on the degree of interest becomes appropriate, as in the above-described first embodiment. The determination of the treatment state is not limited to that based on the treatment state information recorded in the accessory information 101, and may be a determination using image processing on the endoscopic image 100. If the treatment tool 150 and the resection scar 151 of the lesion portion LS are detected by pattern matching, for example, it may be determined that treatment is being performed and that treatment has been performed, respectively.

Modification 2-1

In the above-described first and second embodiments, the degrees of similarity between a medical image of interest and the preceding and subsequent endoscopic images, or the state of treatment for an abnormal region is used as the degree of interest of the user estimated by the section-of-interest setting unit 142. The present invention is not limited thereto, and the degree of abnormality of an abnormal region may be used as the degree of interest to be estimated by the section-of-interest setting unit 142. In this case, the degree of abnormality of an abnormal region is determined by image processing on the basis of, for example, color information, the shape, the size, or the like of the abnormal region. In the case of determining the degree of abnormality from the size of the abnormal region, it is preferable that the dimension of the abnormal region be measured by the endoscope system 16 having a length measurement function, and that the dimension be recorded in the accessory information 101.

Third Embodiment

Figure 18:
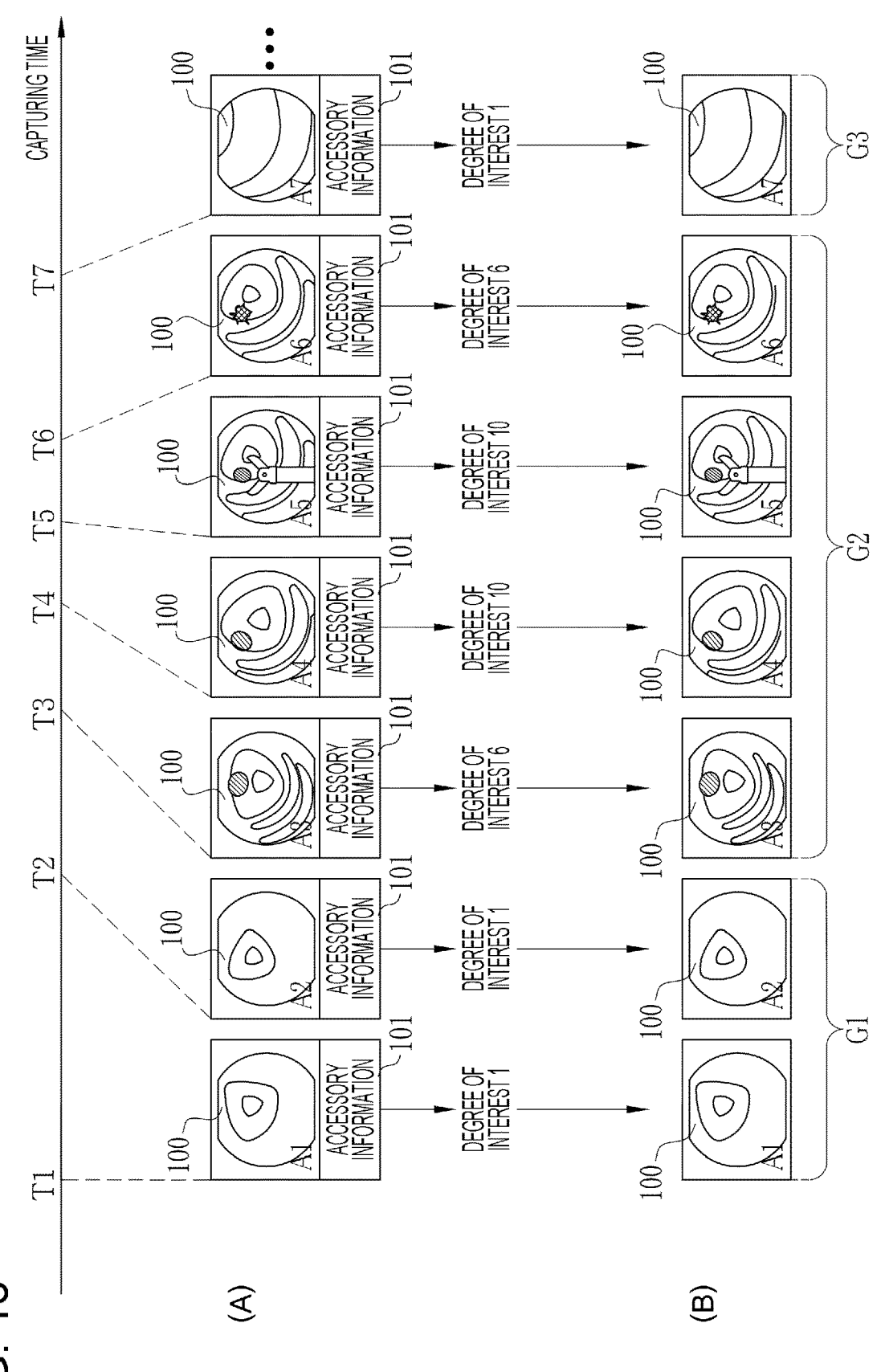
FIG. 18 is an explanatory diagram of estimating the degrees of interest from a plurality of medical images in a third embodiment.

In the above-described first and second embodiments, the degree of interest of the user is estimated by the section-of-interest setting unit 142 on the basis of information on an abnormal region. Alternatively, a value inversely proportional to the capturing interval with respect to the preceding and subsequent endoscopic images in an arrangement in a chronological order may be used as the degree of interest to be estimated. In FIG. 18, capturing times at which endoscopic images are captured are acquired in an endoscopic examination, and the acquired capturing times are recorded in the accessory information 101. Imaging times T1 to T7 in the figure correspond to the image IDs (A1 to A7) of the endoscopic images 100. The third embodiment is similar to the above-described first embodiment except that a value inversely proportional to the imaging interval with respect to the preceding and subsequent endoscopic images 100 is used as the degree of interest to be estimated, and the description will be omitted.

First, in response to receipt of a distribution request from the client terminal 81, the endoscopic image acquiring unit 141 reads out and acquires a plurality of endoscopic images 100 acquired in one endoscopic examination, and accessory information 101 recorded in association with the endoscopic images 100, from the image DB 90 as in the above-described first embodiment.

Subsequently, as illustrated in part (A) of FIG. 18, the section-of-interest setting unit 142 estimates the degrees of interest from the accessory information 101. In the present embodiment, a capturing interval with respect to the preceding and subsequent endoscopic images 100 is calculated from capturing times T1 and T7 recorded as the accessory information 101, and a value inversely proportional to the capturing interval is used as the degree of interest. That is, for the endoscopic images 100 having image IDs A1, A2, and A7 and having a large capturing interval with respect to the preceding and subsequent endoscopic images 100, it is estimated that the degree of interest is 1, which is the lowest. Part (A) of FIG. 18 illustrates an example in which a plurality of endoscopic images 100 of the unit of examination acquired in one endoscopic examination are arranged in a chronological order, in which the endoscopic images 100 having an image ID A8 or thereafter are omitted for the convenience of illustration.

On the other hand, for the endoscopic images 100 having image IDs A3 to A6 and having a small capturing interval with respect to the preceding and subsequent endoscopic images 100, the section-of-interest setting unit 142 estimates that the degree of interest is high. The degree of interest is 6 for the endoscopic images 100 having image IDs A3 and A6, and the degree of interest is 10, which is the highest, for the endoscopic images 100 having image IDs A4 and A5.

Subsequently, the section-of-interest setting unit 142 sets sections of interest to which the plurality of endoscopic images 100 are classified in accordance with the calculated degrees of interest. In the example illustrated in part (B) of FIG. 18, the endoscopic images 100 having image IDs A1 and A2 are classified into a section of interest G1, the endoscopic images 100 having image IDs A3 to A6 are classified into a section of interest G2, and the endoscopic image 100 having an image ID A7 is classified into a section of interest G3, in accordance with the degrees of interest. The classification according to the degrees of interest by the section-of-interest setting unit 142 is similar to that in the above-described first embodiment. The section-of-interest setting unit 142 outputs the set sections of interest and the degrees of interest of the individual endoscopic images to the endoscopic image selecting unit 143.

As described above, by using a value inversely proportional to the capturing interval with respect to the preceding and subsequent endoscopic images 100 as the degree of interest to be estimated, the degree of interest of the user can be estimated more accurately, and the ratio of the selected endoscopic images 100S based on the degree of interest becomes appropriate, as in the first and second embodiments.

The present embodiment can be combined with the above-described first and second embodiments, that is, use of a value inversely proportional to a capturing interval as the degree of interest in the third embodiment can be combined with the estimation of the degree of interest using image processing in the above-described first and second embodiments. For example, it may be possible to use the degree of interest obtained by adding the degree of interest estimated by image processing from the accessory information 101 on an abnormal region in the first and second embodiments, and the degree of interest which is a value inversely proportional to the capturing interval with respect to the preceding and subsequent endoscopic images in the third embodiment, classify a section of interest in accordance with the obtained degree of interest, and select endoscopic images 100 at a ratio based on the obtained degree of interest.

Fourth Embodiment

Figure 19:
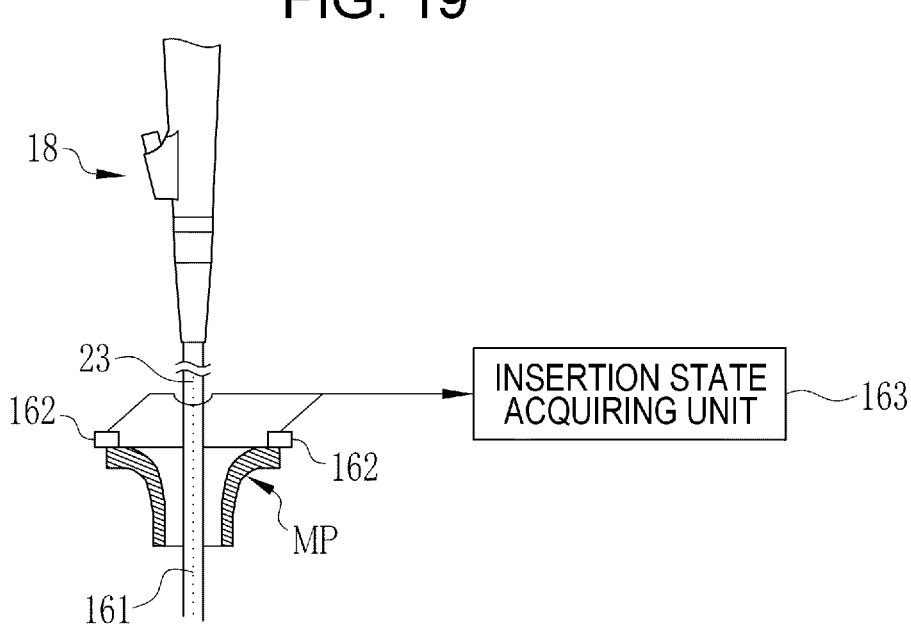
FIG. 19 is a schematic diagram of the configuration of acquiring an insertion length of an insertion section in a fourth embodiment.
Figure 20:
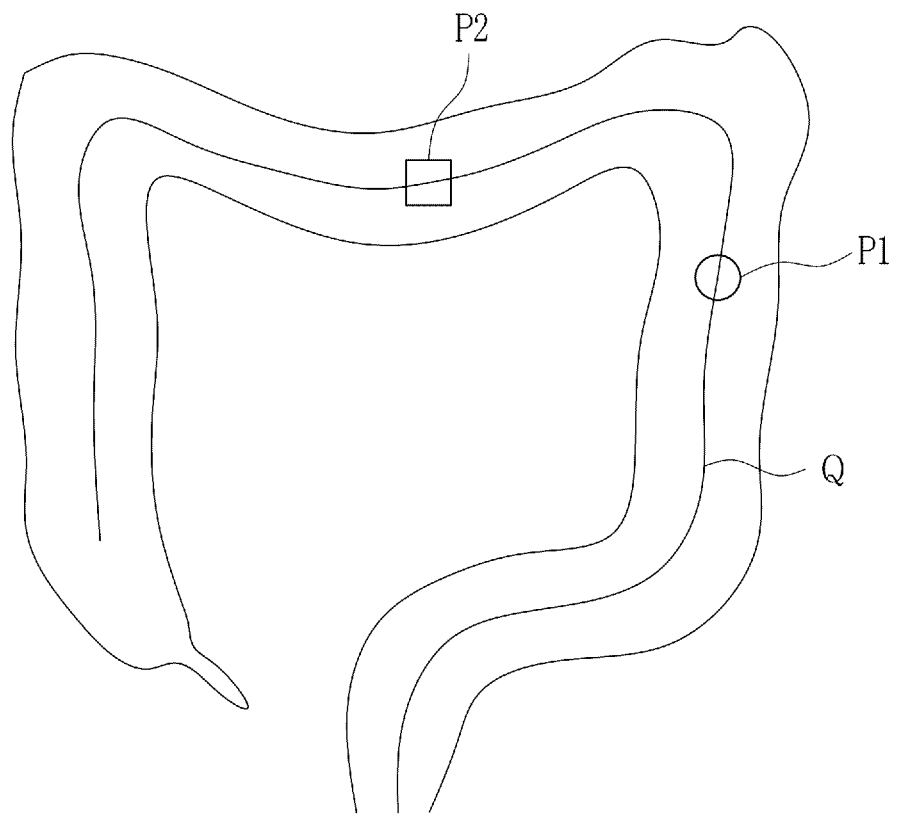
FIG. 20 is an explanatory diagram illustrating a method of acquiring an insertion state of the insertion section of an endoscope in the fourth embodiment.

The estimation of the degree of interest is not limited to the above-described first to third embodiments. When an endoscopic image is captured, position information indicating the position in a subject where an imaging sensor is located may be acquired, the number of times of capturing in which the imaging sensor captures an endoscopic image at the same position may be counted from the position information, and the number of times of capturing may be used as the degree of interest. FIG. 19 and FIG. 20 illustrate a part of an endoscope system that acquires position information indicating the position in a subject where an imaging sensor is located when an endoscopic image is captured in an endoscopic examination. Such an endoscope system that acquires position information is described in detail in WO2018/179991A1 (corresponding to US2020/008653A1). The endoscope system of the fourth embodiment is similar to the endoscope system 16 of the above-described first to third embodiments except for the configuration of acquiring position information indicating a position in a subject, and the description will be omitted.

As illustrated in FIG. 19, measuring graduations 161 for measuring an insertion length of the insertion section 23 in a subject are marked on the outer surface of the insertion section 23 of the endoscope 18. A graduation detection sensor 162 for detecting the measuring graduations 161 is provided at the mouth (in the case of upper endoscopy) or the anus (in the case of lower endoscopy) of a patient. In the example illustrated in FIG. 19, the graduation detection sensor 162 is provided on a mouthpiece MP held by the mouth of a patient. The graduation detection sensor 162 detects the measuring graduations 161 to acquire an insertion length of the insertion section 23. The graduation detection sensor 162 is connected to the processor apparatus 20 in a wired or wireless manner, and transmits an insertion length of the insertion section 23 to an insertion state acquiring unit 163 of the processor apparatus 20.

As illustrated in FIG. 20, the insertion state acquiring unit 163 detects the position of the distal end portion 23a corresponding to the insertion length of the insertion section 23 in a diagnosis path Q along which the insertion section 23 is moved forward and backward in the subject, thereby acquiring a detection position of the distal end portion 23a (i.e., the position of the imaging sensor 39). A detection position of the distal end portion 23a is acquired every time an insertion length of the insertion section 23 is measured. Reference symbols P1 and P2 denote detection positions of the distal end portion 23a. The detection position P2 of the distal end portion 23a is behind the detection position P1 of the distal end portion 23a in the subject. That is, the insertion length at the detection position P2 is greater than the insertion length at the detection position P1.

In the present embodiment, a detection position of the distal end portion 23a is acquired by using an insertion length of the insertion section 23. Alternatively, for example, a magnetic sensor (not illustrated) may be provided on the insertion section 23, and information acquired by the magnetic sensor may be used to acquire a detection position of the distal end portion 23a, shape information of the insertion section 23, and so forth. Alternatively, an X-ray image acquired by capturing an image of a subject using X rays may be used to acquire a detection position of the distal end portion 23a.

As described above, when an endoscopic image is captured, acquired position information is recorded in the accessory information 101 by the endoscope system that acquires the position information indicating a position in the subject where the distal end portion 23a (the imaging sensor 39) is located. As in the above-described embodiments, in response to receipt of a distribution request from the client terminal 81, the endoscopic image acquiring unit 141 reads out and acquires a plurality of endoscopic images 100 acquired in one endoscopic examination, and the accessory information 101 recorded in association with the endoscopic images 100, from the image DB 90.

Figure 21:
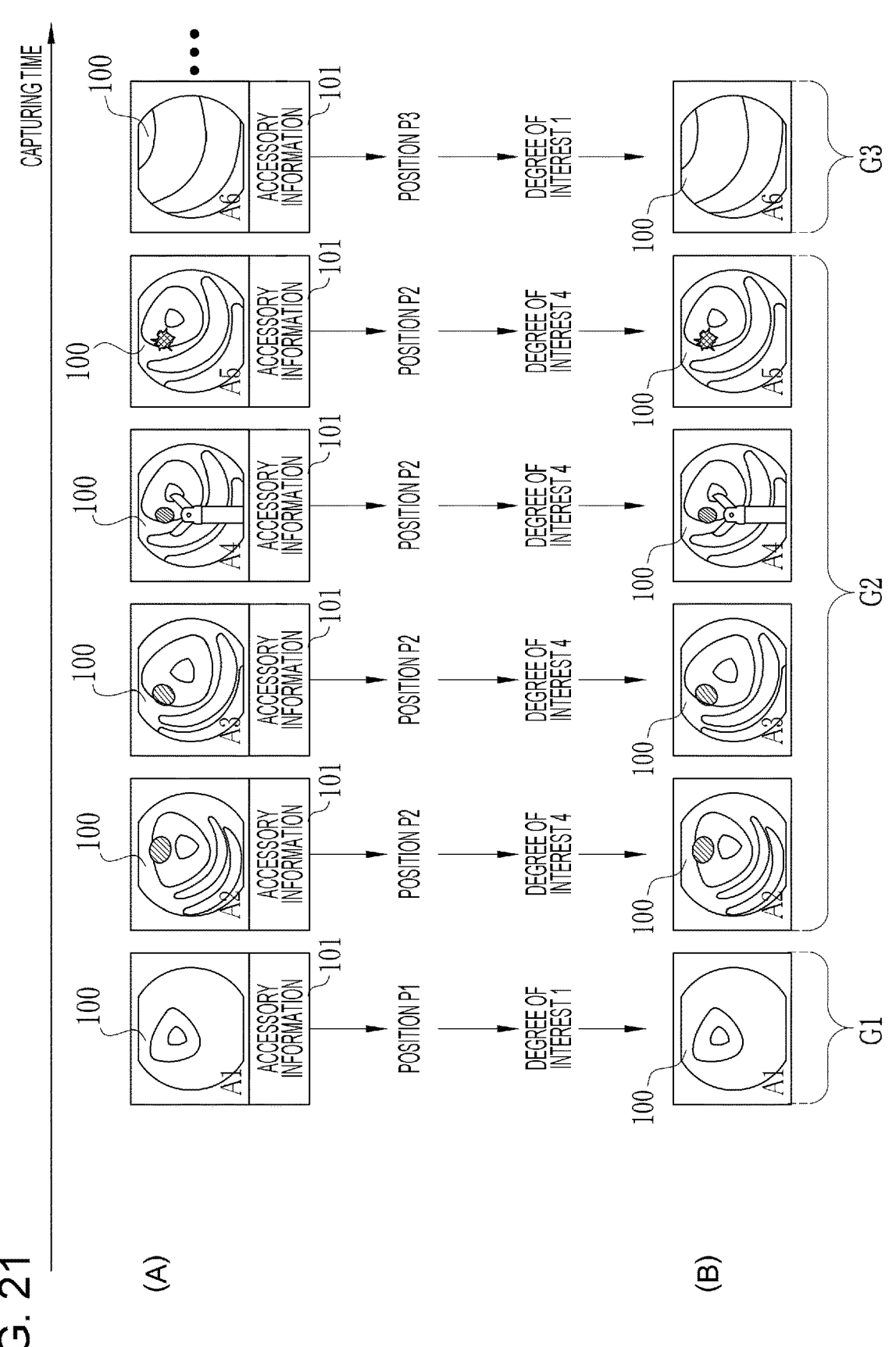
FIG. 21 is an explanatory diagram of estimating the degrees of interest from a plurality of medical images in the fourth embodiment.

Subsequently, as illustrated in part (A) of FIG. 21, the section-of-interest setting unit 142 estimates the degrees of interest from the accessory information 101. In the present embodiment, the number of times of capturing in which the imaging sensor 39 captures an endoscopic image at the same position is counted from the position information recorded as the accessory information 101, and the number of times of capturing is used as the degree of interest. That is, for the endoscopic images 100 having image IDs A1 and A6 in which the number of times of capturing performed by the imaging sensor 39 at the same position is small, the numbers of times of capturing at the positions P1 and P3 are both one, and thus it is estimated that the degree of interest is 1, which is the lowest. Part (A) of FIG. 21 illustrates an example in which a plurality of endoscopic images 100 of the unit of examination acquired in one endoscopic examination are arranged in a chronological order, in which the endoscopic images 100 having an image ID A7 or thereafter are omitted for the convenience of illustration.

On the other hand, for the endoscopic images 100 having image IDs A2 to A5 in which the number of times of capturing performed by the imaging sensor 39 at the same position is large, the section-of-interest setting unit 142 estimates that the degree of interest is 4, which is the highest, because the number of times of capturing at the position P2 is four.

Subsequently, the section-of-interest setting unit 142 sets sections of interest to which the plurality of endoscopic images 100 are classified in accordance with the calculated degrees of interest. In the example illustrated in part (B) of FIG. 21, the endoscopic image 100 having an image ID A1 is classified into a section of interest G1, the endoscopic images 100 having image IDs A2 to A5 are classified into a section of interest G2, and the endoscopic image 100 having an image ID A6 is classified into a section of interest G3, in accordance with the degrees of interest. The classification according to the degrees of interest by the section-of-interest setting unit 142 is similar to that in the above-described first embodiment. The section-of-interest setting unit 142 outputs the set sections of interest and the degrees of interest of the individual endoscopic images to the endoscopic image selecting unit 143.

As described above, as a result of counting the number of times of capturing in which the imaging sensor 39 captures an endoscopic image at the same position and using the number of times of capturing as the degree of interest to be estimated, the degree of interest of the user can be estimated more accurately, and the ratio of the selected endoscopic images 100S based on the degree of interest becomes appropriate, as in the above-described first to third embodiments.

The present embodiment can be combined with the above-described first and second embodiments, that is, use of the number of times of capturing as the degree of interest in the fourth embodiment can be combined with the estimation of the degree of interest using image processing in the above-described first and second embodiments. For example, it may be possible to use the degree of interest obtained by adding the degree of interest estimated by image processing from the accessory information 101 on an abnormal region in the first and second embodiments, and the degree of interest which is the number of times of capturing obtained by counting the number of times of capturing in which the imaging sensor 39 captures an endoscopic image at the same position in the fourth embodiment, classify a section of interest in accordance with the obtained degree of interest, and select endoscopic images 100 at a ratio based on the obtained degree of interest.

Modification 4-1

In the above-described fourth embodiment, when an endoscopic image is captured, position information indicating a position in a subject where an imaging sensor is located is acquired, the number of times of capturing in which the imaging sensor captures an endoscopic image at the same position is counted from the position information, and the number of times of capturing is used as the degree of interest. Alternatively, when an endoscopic image is captured, the degree of interest may be estimated from position information indicating a position in a subject where the imaging sensor is located and information on a capturing time. In the present modification, a capturing time is recorded in the accessory information 101 as in the above-described third embodiment, and position information indicating a position in a subject where the imaging sensor is located is recorded in the accessory information 101 as in the above-described fourth embodiment.

The section-of-interest setting unit 142 estimates the degree of interest from the accessory information 101 in which the capturing time and the position information are recorded as described above. In this case, it is preferable that the section-of-interest setting unit 142 acquire the position information and the capturing time, and use the length of stay time during which the imaging sensor stays at the same position as the degree of interest when an endoscopic image is captured. This is because the stay time of the imaging sensor is naturally long at a place where the doctor needs to concentrate and carefully perform an examination. In this case, it is possible to determine, from the position information, that the endoscopic images have been captured when the imaging sensor stays at the same position, and calculate the stay time from the difference in the capturing time between the endoscopic images captured when the imaging sensor stays at the same position.

As described above, as a result of using, as the degree of interest to be estimated, the length of stay time during which the imaging sensor stays at the same position when the endoscopic images are captured, the degree of interest of the user can be estimated more accurately, and the ratio of the selected endoscopic images 100S based on the degree of interest becomes appropriate, as in the above-described embodiments. Like the above-described fourth embodiment, the present modification can be combined with the above-described first and second embodiments.

Fifth Embodiment

Figure 22:
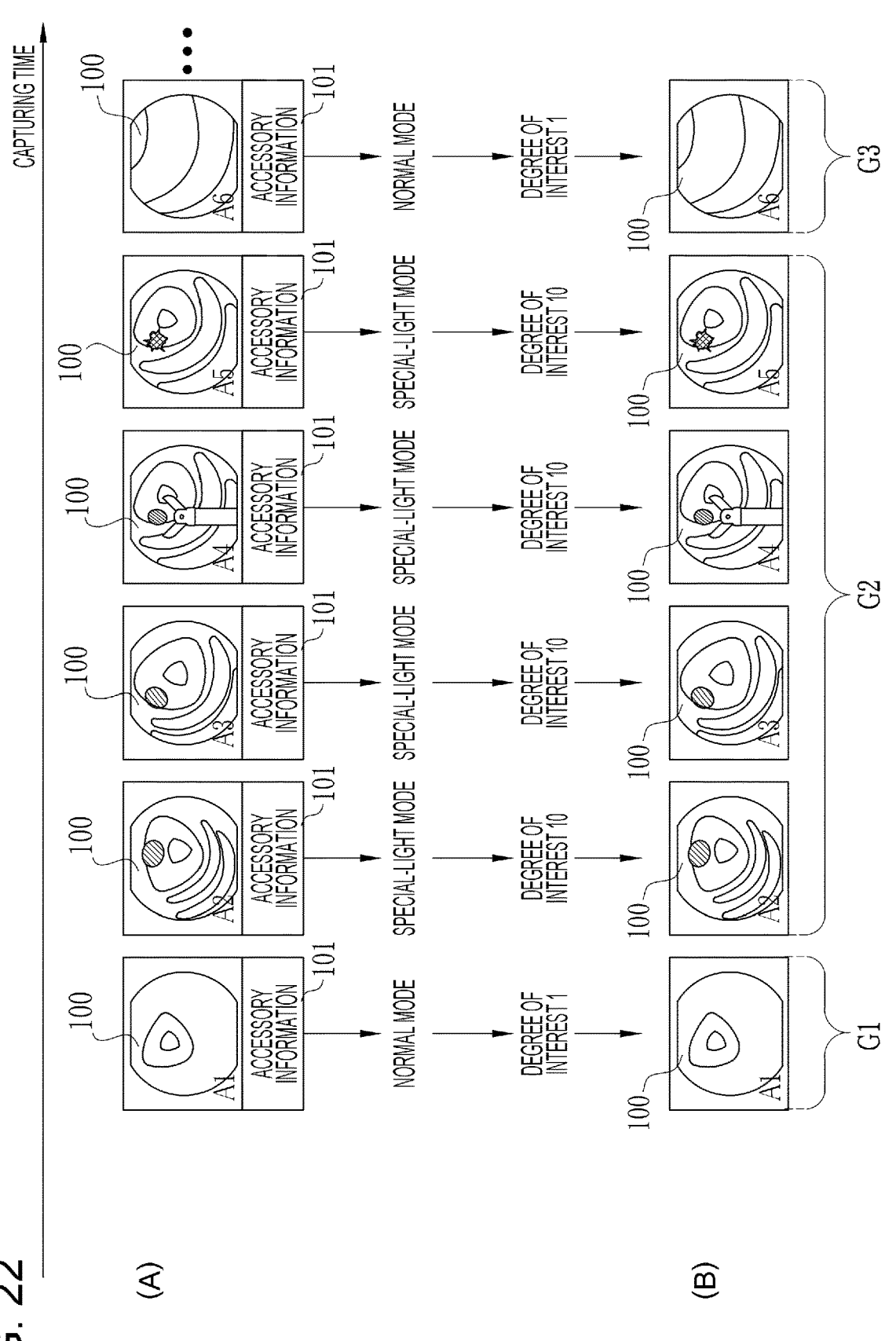
FIG. 22 is an explanatory diagram of estimating the degrees of interest from a plurality of medical images in a fifth embodiment.

The estimation of the degree of interest is not limited to the above-described first to fourth embodiments. Wavelength range information of a light source used to capture an endoscopic image may be acquired, and the degree of interest may be estimated from the wavelength range information of the light source. In FIG. 22, the type of observation mode selected at the time of capturing an endoscopic image is acquired as wavelength range information of the light source used to capture the endoscopic image in an endoscopic examination, and the acquired type of observation mode is recorded in the accessory information 101. The fifth embodiment is similar to the above-described first embodiment except that the degree of interest is estimated from wavelength range information of the light source, and the description will be omitted.

First, in response to receipt of a distribution request from the client terminal 81, the endoscopic image acquiring unit 141 reads out and acquires a plurality of endoscopic images 100 acquired in one endoscopic examination, and accessory information 101 recorded in association with the endoscopic images 100, from the image DB 90 as in the above-described first embodiment.

Subsequently, as illustrated in part (A) of FIG. 22, the section-of-interest setting unit 142 estimates the degrees of interest from the accessory information 101. In the present embodiment, the degree of interest is estimated from the type of observation mode selected as the accessory information 101 at the time of capturing an endoscopic image. That is, for the endoscopic images 100 having image IDs A1 and A6 in which the observation mode is the normal mode, it is estimated that the degree of interest is 1, which is the lowest. Part (A) of FIG. 22 illustrates an example in which a plurality of endoscopic images 100 of the unit of examination acquired in one endoscopic examination are arranged in a chronological order, in which the endoscopic images 100 having an image ID A7 or thereafter are omitted for the convenience of illustration.

On the other hand, for the endoscopic images 100 having image IDs A2 to A5 in which the observation mode is the special-light mode, the section-of-interest setting unit 142 estimates that the degree of interest is 10, which is the highest. As described above, the special-light mode uses special light having a wavelength range different from that of the normal light used in the normal mode. Use of the special light to capture an endoscopic image increases the resolution of a blood vessel structure or a gland duct structure. Thus, it is estimated that the user has a target to be observed in the special-light mode, that is, the degree of interest is high.

Subsequently, the section-of-interest setting unit 142 sets sections of interest to which the plurality of endoscopic images 100 are classified in accordance with the calculated degrees of interest. In the example illustrated in part (B) of FIG. 22, the endoscopic image 100 having an image ID A1 is classified into a section of interest G1, the endoscopic images 100 having image IDs A2 to A5 are classified into a section of interest G2, and the endoscopic image 100 having an image ID A6 is classified into a section of interest G3, in accordance with the degrees of interest. The classification according to the degrees of interest by the section-of-interest setting unit 142 is similar to that in the above-described first embodiment. The section-of-interest setting unit 142 outputs the set sections of interest and the degrees of interest of the individual endoscopic images to the endoscopic image selecting unit 143.

As described above, as a result of estimating the degree of interest from wavelength range information of the light source, the degree of interest of the user can be estimated more accurately, and the ratio of the selected endoscopic images 100S based on the degree of interest becomes appropriate, as in the above-described first and second embodiments.

The present embodiment can be combined with the above-described first and second embodiments, that is, the degree of interest estimated from wavelength range information of a light source in the fifth embodiment can be combined with the estimation of the degree of interest using image processing in the above-described first and second embodiments. For example, it may be possible to use the degree of interest obtained by adding the degree of interest estimated by image processing from the accessory information 101 on an abnormal region in the first and second embodiments, and the degree of interest estimated from wavelength range information of a light source in the fifth embodiment, classify a section of interest in accordance with the obtained degree of interest, and select endoscopic images 100 at a ratio based on the obtained degree of interest.

Modification 5-1

In the above-described embodiments, the endoscopic image selecting unit 143 selects an endoscopic image 100 from each section of interest at the ratio based on the degree of interest. Alternatively, if the number of images based on the ratio exceeds the number designated by the user, endoscopic images may be selected within a range not exceeding the number designated by the user. In this modification, an upper limit number of endoscopic images to be selected can be input in the endoscopic image viewing support server 80.

Figure 23:
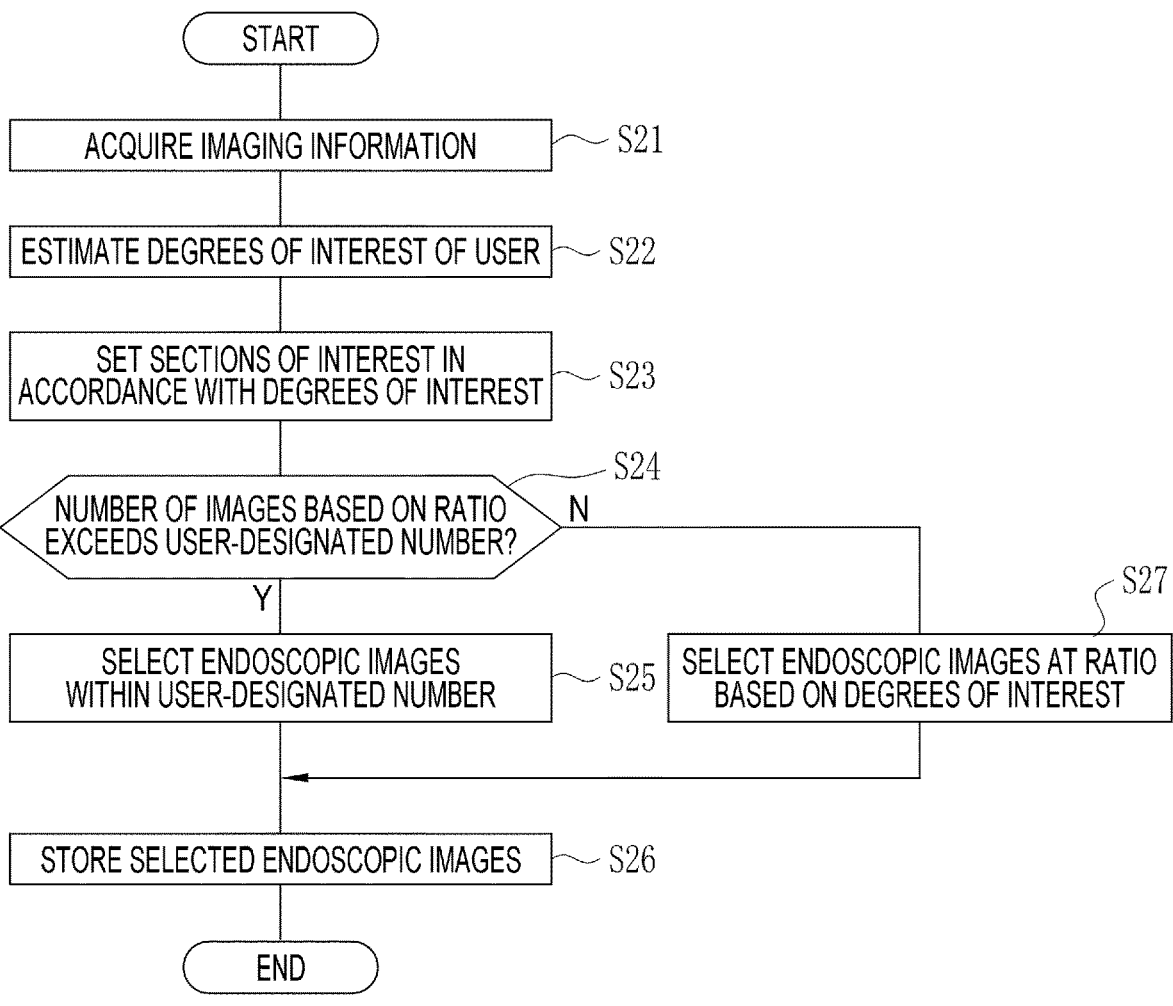
FIG. 23 is a flowchart illustrating a processing procedure in a modification 5-1 of the present invention.

In the present modification, as illustrated in FIG. 23, the endoscopic image selecting unit 143 calculates a ratio based on the degree of interest, and determines whether the number based on the ratio exceeds a user-designated number in each section of interest (S24). S21 to S23 in the flowchart in FIG. 23 are the same as S11 to S13 in the flowchart in FIG. 14 of the above-described first embodiment, and the description thereof will be omitted.

If the number based on the ratio exceeds the user-designated number (Y in S24), the endoscopic image selecting unit 143 selects endoscopic images 100 within the user-designated number for the corresponding section of interest (S25). The selected endoscopic images 100S selected from the section of interest within the user-designated number are output to the screen display control unit 144 and the storage control unit 145. The storage control unit 145 causes the image DB 90 to store the selected endoscopic images 100S (S26).

On the other hand, if the number based on the ratio does not exceed the user-designated number (N in S24), the endoscopic image selecting unit 143 selects endoscopic images 100 at the ratio based on the degree of interest for the corresponding section of interest (S27). The selected endoscopic images 100S selected from the section of interest at the ratio based on the degree of interest are output to the screen display control unit 144 and the storage control unit 145. The storage control unit 145 causes the image DB 90 to store the selected endoscopic images 100S (S26).

Modification 5-2

Figure 24:
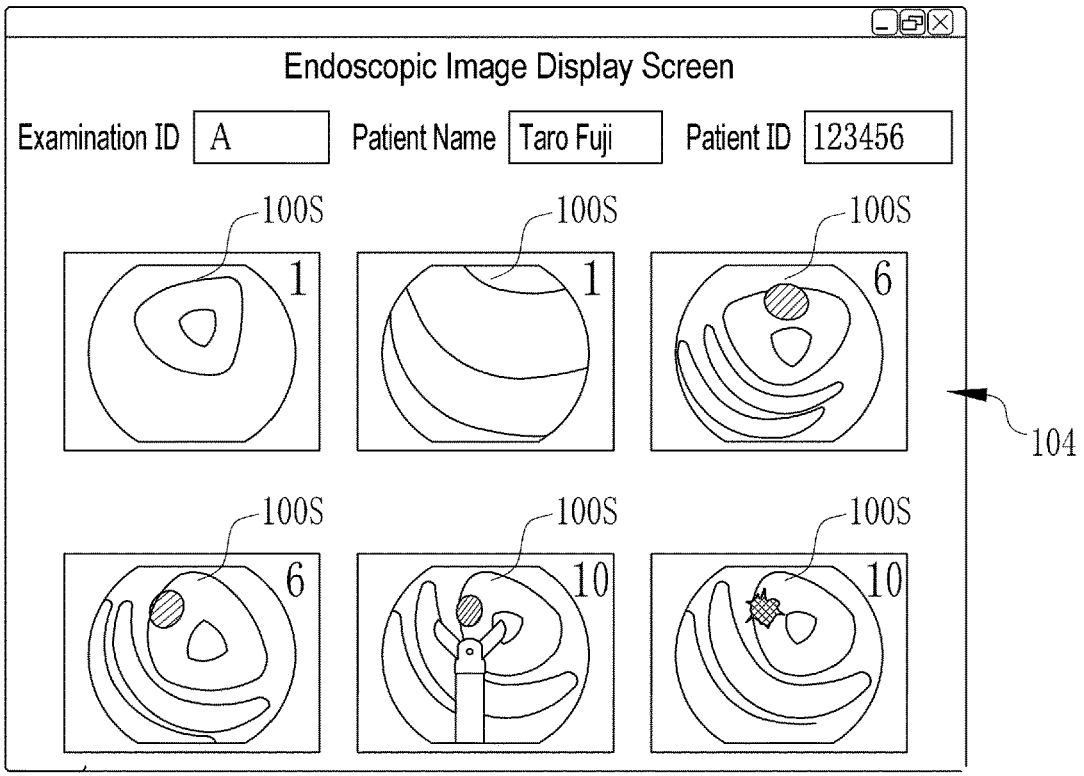
FIG. 24 is an explanatory diagram illustrating the contents of an endoscopic image display screen in a modification 5-2 of the present invention.

On the endoscopic image display screen 104 in the above-described embodiments, only the selected endoscopic images 100S selected by the endoscopic image selecting unit 143 are displayed in a chronological order, but the present invention is not limited thereto. As illustrated in FIG. 24, the selected endoscopic images 100S may be displayed in order of the degree of interest calculated by the section-of-interest setting unit 142. In FIG. 24, the number attached to each selected endoscopic image 100S indicates the degree of interest. The selected endoscopic images 100S are arranged in order of the degree of interest from the upper left toward the lower right. In the example illustrated in FIG. 24, the degree of interest is attached to all the selected endoscopic images 100S. These degrees of interest may or may not be displayed, or may be displayed only when the degree of interest is higher than or equal to a certain threshold value.

Modification 5-3

Figure 25:
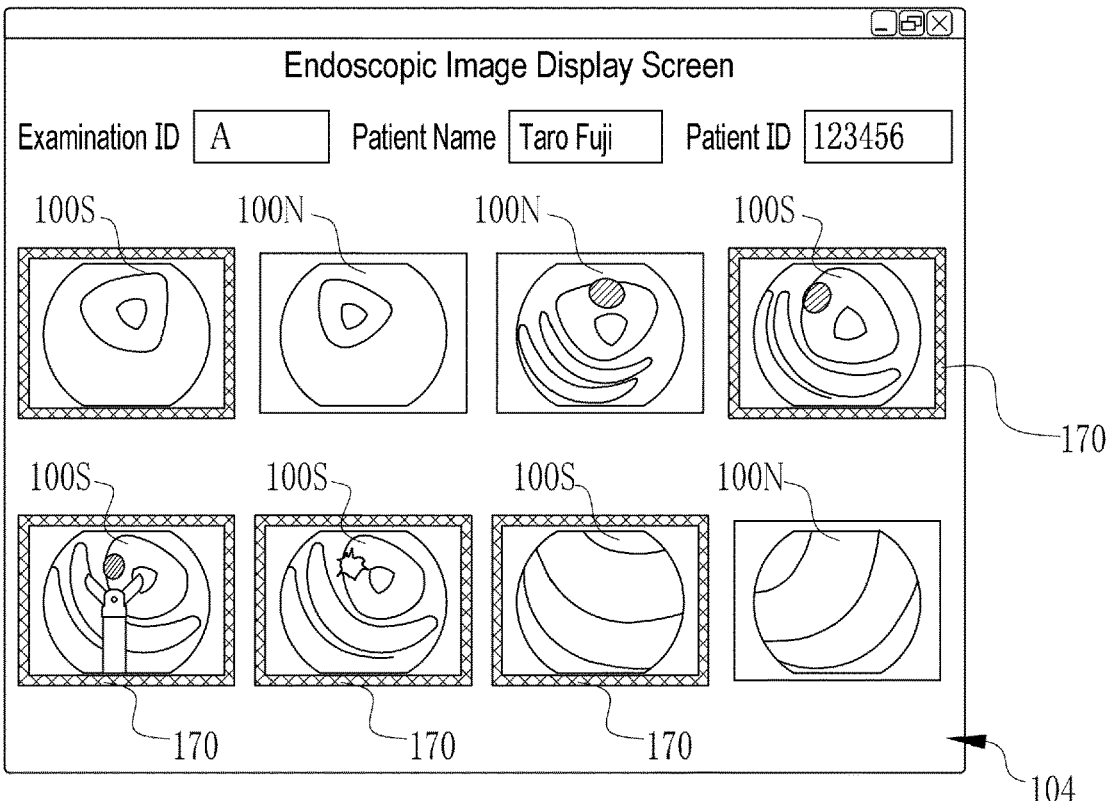
FIG. 25 is an explanatory diagram illustrating the contents of an endoscopic image display screen in a modification 5-3 of the present invention.

As well as the selected endoscopic image display mode of displaying only the selected endoscopic images 100S, an all images display mode of displaying all of a plurality of endoscopic images 100 acquired in one endoscopic examination may be performed in the endoscopic image display screen 104 as illustrated in FIG. 25. In this case, it is preferable that the selected endoscopic images 100S and the non-selected endoscopic images 100N, which are the endoscopic images 100 not selected, be displayed differently so that the user is able to distinguish them. In the example illustrated in FIG. 25, the selected endoscopic images 100S are displayed with an outer frame 170. Alternatively, the selected endoscopic images 100S and the non-selected endoscopic images 100N may be displayed differently, for example, by using different background colors. In the example illustrated in FIG. 25, the non-selected endoscopic images 100N are displayed in a chronological order in addition to the selected endoscopic images 100S. Alternatively, the images may be displayed in order of the degree of interest. Also in such an all images display mode, the degree of interest may or may not be displayed, or may be displayed only when the degree of interest is higher than or equal to a certain threshold value.

In the above example, the endoscopic image display screen 104 in the selected endoscopic image display mode and the endoscopic image display screen 104 in the all images display mode are separately displayed. Alternatively, the endoscopic image display screen 104 in the selected endoscopic image display mode and the endoscopic image display screen 104 in the all images display mode may be displayed in one screen. The display mode may be switched for display by a user operation.

In the above-described embodiments, only still images of endoscopic images acquired by operating the freeze switch 24*b* by the user are targets of acquisition of endoscopic images, estimation of the degree of interest, and selection and storage of endoscopic images in the endoscopic image viewing support server 80. However, the present invention is not limited thereto. An endoscopic image automatically acquired without a user operating the endoscope system, for example, an endoscopic image captured as a moving image (frames constituting a moving image) may be acquired, and estimation of the degree of interest, and selection and storage of the endoscopic image may be performed. Alternatively, endoscopic images captured at a preset capturing interval, or an endoscopic image having a feature quantity similar to that of an image preset by a neural network or the like may be acquired.

Although an observation target is illuminated by using the four-color LEDs 30*a* to 30*d* in the above-described embodiments, the observation target may be illuminated by using a laser light source and a fluorescent body. Although an observation target is illuminated by using the four-color LEDs 30*a* to 30*d* in the above-described embodiments, the observation target may be illuminated by using a white light source such as a xenon lamp and a rotary filter. Imaging of an observation target may be performed by using a monochrome imaging sensor instead of the color imaging sensor 39.

In the above-described embodiments, the medical image processing apparatus of the present invention is applied to an endoscope system that acquires an endoscopic image as a medical image. However, the medical image processing apparatus of the present invention can obviously be applied to various endoscope systems, such as a capsule endoscope. The medical image processing apparatus of the present invention can also be applied to various medical image apparatuses that acquire X-ray images, CT images, MR images, ultrasound images, pathological images, positron emission tomography (PET) images, and the like as other medical images.

In the above-described embodiments, the hardware structure of a processing unit that executes various processing operations, such as the endoscopic image acquiring unit 141, the section-of-interest setting unit 142, the endoscopic image selecting unit 143, the screen display control unit 144, the storage control unit 145, and the image data generating unit 146, may be various types of processors described below. The various types of processors include a central processing unit (CPU), which is a general-purpose processor executing software (program) and functioning as various processing units; a graphical processing unit (GPU); a programmable logic device (PLD), which is a processor whose circuit configuration is changeable after manufacturing, such as a field programmable gate array (FPGA); a dedicated electric circuit, which is a processor having a circuit configuration designed exclusively for executing various processing operations, and the like.

A single processing unit may be constituted by one of these various types of processors or may be constituted by a combination of two or more processors of the same type or different types (for example, a combination of a plurality of FPGAs, a combination of a CPU and an FPGA, or a combination of a CPU and a GPU). A plurality of processing units may be constituted by a single processor. Examples of constituting a plurality of processing units by a single processor are as follows. First, as represented by a computer of a client or server, a single processor is constituted by a combination of one or more CPUs and software, and the processor functions as a plurality of processing units. Secondly, as represented by a system on chip (SoC), a processor in which a single integrated circuit (IC) chip implements the function of an entire system including a plurality of processing units is used. In this way, various types of processing units are constituted by using one or more of the above-described various types of processors as a hardware structure.

Furthermore, the hardware structure of the various types of processors is, more specifically, electric circuitry formed by combining circuit elements such as semiconductor elements.

REFERENCE SIGNS LIST

10 endoscopic image viewing support system
14 network
16 endoscope system
18 endoscope
19 light source apparatus
20 processor apparatus
21 display
22 console
23 insertion section
23*a* distal end portion
23*b* bending portion
24 operation section
24*a* angle knob
24*b* freeze switch
24*c* mode switching unit
24*d* zoom operation unit
30 light source unit
30*a* V-LED
30*b* B-LED
30*c* G-LED
30*d* R-LED
31 light source control unit
32 wavelength cut filter
33 light guide
35*a* illumination optical system
35*b* imaging optical system
36 illumination lens
37 objective lens
38 magnifying optical system
38*a* zoom lens
38*b* lens driving unit
39 imaging sensor
40 CDS circuit

US 12,694,529 B2

31

42 AGC circuit
44 A/D conversion circuit
50 image signal acquiring unit
51 digital signal processor (DSP)
52 noise reducing unit
53 image processing unit
54 display control unit
55 image storage control unit
56 image storage unit
58 normal-mode image processing unit
59 special-light-mode image processing unit
60 abnormal-region-detection-mode image processing unit
61 image-for-detection processing unit
62 abnormal region detecting unit
80 endoscopic image viewing support server
81 client terminal
82 server group
84 network
86 image server
88 report server
90 image database
92 report database
94 examination report
94A report main body
96 image folder
98 report folder
100 endoscopic image
100A endoscopic image of interest
100N non-selected endoscopic image
100S selected endoscopic image
101 accessory information
101A detection information
102 imaging information
104 endoscopic image display screen
104A switch button
105 findings
106 report display screen
108 pointer
110 central processing unit (CPU)
112 memory
114 storage device
118 input/output unit
120 data bus
122 display
124 input device
126 application program
128 startup screen
128A input field
128B OK button
130 graphical user interface (GUI) control unit
132 request issuing unit
140 receiving unit
141 endoscopic image acquiring unit
142 section-of-interest setting unit
143 endoscopic image selecting unit
144 screen display control unit
145 storage control unit
146 screen data generating unit
147 output control unit
150 treatment tool
151 resection scar
161 measuring graduations
162 graduation detection sensor
163 insertion state acquiring unit
170 outer frame

32

A examination
G1, G2, G3 section of interest
Q diagnosis path
T1 to T7 capturing time

What is claimed is:

1. A medical image processing apparatus comprising a processor with a memory configured to:
acquire imaging information that has a plurality of medical images captured by a user using an imaging sensor and that has accessory information recorded in association with each medical image, the accessory information including at least one of capturing time information indicating a time at which each medical image is captured, and position information indicating a position of the imaging sensor when each medical image is captured;
estimate, from the imaging information, a degree of interest of the user when the medical image is captured, the estimating of the degree of interest including:
determining movement of the imaging sensor on the basis of at least one of the capturing time information and the position information, the movement of the imaging sensor being evaluated using at least one of (a) an imaging interval between adjacent medical images, (b) a staying time of the imaging sensor at a same position, and (c) a number of medical images captured at the same position; and
calculating the degree of interest based on the movement of the imaging sensor;
set sections of interest to which the plurality of medical images are classified in accordance with the degree of interest;
select a medical image from each section of interest at a ratio that is based on the degree of interest; and
determine a medical image of interest from among the plurality of medical images on the basis of the imaging information, and in a case where the plurality of medical images are arranged in a chronological order, estimate the degree of interest for at least one medical image in a medical image group including the medical image of interest by using image processing, wherein
the medical image is an endoscopic image captured by an imaging sensor of an endoscope,
the accessory information has, recorded therein, position information indicating a position in a subject where the imaging sensor is located when the medical image is captured, and a capturing time at which the medical image is captured, and
the processor is configured to acquire the position information and the capturing time, and use, as the degree of interest, a length of a stay time during which the imaging sensor stays at the same position when the medical image is captured.

2. The medical image processing apparatus according to claim 1, wherein the processor is configured to, in the estimation of the degree of interest using image processing, use, as the degree of interest, a degree of similarity with preceding and subsequent medical images in an arrangement in a chronological order.

3. The medical image processing apparatus according to claim 1, wherein the processor is configured to:
determine a medical image including an abnormal region to be the medical image of interest; and
in the estimation of the degree of interest using image processing, use, as the degree of interest, a degree of abnormality of the abnormal region.

4. The medical image processing apparatus according to claim 1, wherein the processor is configured to:

determine a medical image including an abnormal region to be the medical image of interest; and in the estimation of the degree of interest using image processing, use, as the degree of interest, a state of treatment for the abnormal region.

5. The medical image processing apparatus according to claim 1, wherein the processor is configured to:

in addition to perform the estimation of the degree of interest using image processing, use, as the degree of interest, a value inversely proportional to a capturing interval with respect to preceding and subsequent medical images in an arrangement in a chronological order.

6. The medical image processing apparatus according to claim 1, wherein the processor is configured to count, using the position information, the number of times of capturing in which the imaging sensor captures the medical image at the same position, and use the number of times of capturing as the degree of interest.

7. The medical image processing apparatus according to claim 1, wherein the accessory information is wavelength rangeinformation of a light source used to capture the medical image, and the processor is configured to estimate the degree of interest from the wavelength range information.

8. The medical image processing apparatus according to claim 1, wherein the processor is configured to acquire the medical image and the accessory information, the medical image being captured by the user operating a device.

9. The medical image processing apparatus according to claim 1, wherein the processor is configured to acquire the medical image and the accessory information, the medical image being automatically captured without the user operating a device.

10. The medical image processing apparatus according to claim 1, wherein the processor is configured to select the medical image within a range not exceeding the number of images designated by the user.

11. The medical image processing apparatus according to claim 1, wherein the processor is configured to display the selected medical image in an order that is based on the degree of interest.

12. The medical image processing apparatus according to claim 1, wherein the processor is configured to store the selected medical image in a storage device.

13. A method for operating a medical image processing apparatus, the method comprising:

acquiring imaging information that has a plurality of medical images captured by a user using an imaging sensor and that has accessory information recorded in association with each medical image, the accessory information including at least one of capturing time information indicating a time at which each medical image is captured, and position information indicating a position of the imaging sensor when each medical image is captured;

estimating, from the imaging information, a degree of interest of the user when the medical image is captured, the estimating of the degree of interest including:

determining movement of the imaging sensor on the basis of at least one of the capturing time information and the position information, the movement of the imaging sensor being evaluated using at least one of (a) an imaging interval between adjacent medical images, (b) a staying time of the imaging sensor at a same position, and (c) a number of medical images captured at the same position; and calculating the degree of interest based on the movement of the imaging sensor;

setting sections of interest to which the plurality of medical images are classified in accordance with the degree of interest;

selecting a medical image from each section of interest at a ratio that is based on the degree of interest; and determining a medical image of interest from among the plurality of medical images on the basis of the imaging information, and in a case where the plurality of medical images are arranged in a chronological order, estimating the degree of interest for at least one medical image in a medical image group including the medical image of interest by using image processing, wherein the medical image is an endoscopic image captured by an imaging sensor of an endoscope, the accessory information has, recorded therein, position information indicating a position in a subject where the imaging sensor is located when the medical image is captured, and a capturing time at which the medical image is captured, and the method further comprises a step of acquiring the position information and the capturing time, and using, as the degree of interest, a length of a stay time during which the imaging sensor stays at the same position when the medical image is captured.

14. A non-transitory computer readable medium for storing a computer-executable program for performing image processing on a medical image, the computer-executable program causing a computer to implement:

a function of acquiring imaginginformation that has a plurality of medical images captured by a user using an imaging sensor and that has accessory information recorded in association with each medical image, the accessory information including at least one of capturing time information indicating a time at which each medical image is captured, and position information indicating a position of the imaging sensor when each medical image is captured;

a function of estimating, from the imaging information, a degree of interest of the user when the medical image is captured, the estimating of the degree of interest including:

determining movement of the imaging sensor on the basis of at least one of the capturing time information and the position information, the movement of the imaging sensor being evaluated using at least one of (a) an imaging interval between adjacent medical images, (b) a staying time of the imaging sensor at a same position, and (c) a number of medical images captured at the same position; and calculating the degree of interest based on the movement of the imaging sensor;

a function of setting sections of interest to which the plurality of medical images are classified in accordance with the degree of interest;

a function of selecting a medical image from each section of interest at a ratio that is based on the degree of interest; and a function of determining a medical image of interest from among the plurality of medical images on the basis of the imaging information, and in a case where the plurality of medical images are arranged in a chronological order, estimating the degree of interest for at least one medical image in a medical image groupincluding the medical image of interest by using image processing, wherein the medical image is an endoscopic image captured by an imaging sensor of an endoscope, the accessory information has, recorded therein, position information indicating a position in a subject where the imaging sensor is located when the medical image is captured, and a capturing time at which the medical image is captured, and the computer-executable program further causes the computer to implement a function of acquiring the position information and the capturing time, and using, as the degree of interest, a length of a stay time during which the imaging sensor stays at the same position when the medical image is captured.

\*   \*   \*   \*   \*